US012290539B2

(12) United States Patent
Aroian et al.

(10) Patent No.: US 12,290,539 B2
(45) Date of Patent: May 6, 2025

(54) PURIFIED ANTHELMINTIC COMPOSITIONS AND RELATED METHODS

(71) Applicant: UNIVERSITY OF MASSACHUSETTS, Boston, MA (US)

(72) Inventors: Raffi Van Aroian, Worcester, MA (US); Gary R. Ostroff, Worcester, MA (US)

(73) Assignee: UNIVERSITY OF MASSACHUSETTS, Westborough, MA (US)

( * ) Notice: Subject to any disclaimer, the term of this patent is extended or adjusted under 35 U.S.C. 154(b) by 0 days.

(21) Appl. No.: 18/485,796

(22) Filed: Oct. 12, 2023

(65) Prior Publication Data

US 2024/0148800 A1 May 9, 2024

Related U.S. Application Data

(62) Division of application No. 16/607,677, filed as application No. PCT/US2018/033962 on May 22, 2018, now Pat. No. 11,844,815.

(60) Provisional application No. 62/510,081, filed on May 23, 2017.

(51) Int. Cl.
*A61K 35/741* (2015.01)
*A61K 9/48* (2006.01)
*A61K 38/16* (2006.01)
*A61P 33/10* (2006.01)
*A61K 45/06* (2006.01)

(52) U.S. Cl.
CPC .............. *A61K 35/741* (2013.01); *A61K 9/48* (2013.01); *A61K 38/164* (2013.01); *A61P 33/10* (2018.01); *A61K 45/06* (2013.01)

(58) Field of Classification Search
CPC .................................................. A61K 35/741
See application file for complete search history.

(56) References Cited

U.S. PATENT DOCUMENTS

| | | |
|---|---|---|
| 4,865,981 A | 9/1989 | Herrnstadt et al. |
| 5,591,433 A | 1/1997 | Michael et al. |
| 5,596,071 A | 1/1997 | Payne et al. |
| 6,221,648 B1 | 4/2001 | Lepage et al. |
| 7,351,881 B2 | 4/2008 | Carozzi et al. |
| 7,923,602 B2 | 4/2011 | Carozzi et al. |
| 8,809,268 B2 | 8/2014 | Aroian et al. |
| 10,940,170 B2 | 3/2021 | Aroian et al. |
| 11,484,568 B2 | 11/2022 | Aroian et al. |
| 11,826,389 B2 | 11/2023 | Aroian et al. |
| 11,844,815 B2 | 12/2023 | Aroian et al. |
| 2001/0010932 A1 | 8/2001 | Schnepf et al. |
| 2006/0014942 A1 | 1/2006 | Lereclus et al. |
| 2009/0260107 A1 | 10/2009 | English et al. |
| 2010/0024075 A1 | 1/2010 | Aroian et al. |
| 2010/0203521 A1 | 8/2010 | Klapperich et al. |
| 2011/0263489 A1 | 10/2011 | Aroian et al. |
| 2015/0079203 A1 | 3/2015 | Thomas et al. |
| 2017/0348362 A1 | 12/2017 | Aroian et al. |
| 2019/0015474 A1 | 1/2019 | Aroian et al. |
| 2020/0188452 A1 | 6/2020 | Aroian et al. |
| 2021/0268045 A1 | 9/2021 | Aroian et al. |
| 2022/0354905 A1 | 11/2022 | Aroian et al. |
| 2023/0128953 A1 | 4/2023 | Aroian et al. |

FOREIGN PATENT DOCUMENTS

| | | |
|---|---|---|
| CN | 1488615 A | 9/2003 |
| EP | 3630150 A1 | 4/2020 |
| WO | WO 1989/007605 A1 | 8/1989 |
| WO | WO 2006/123157 A2 | 11/2006 |
| WO | WO 2007/062064 A2 | 5/2007 |
| WO | WO 2010/053517 A2 | 5/2010 |
| WO | WO 2016/007355 A1 | 1/2016 |
| WO | WO 2016/100128 A1 | 6/2016 |
| WO | WO 2017/123946 A1 | 7/2017 |
| WO | WO 2018/217807 A1 | 11/2018 |

OTHER PUBLICATIONS

Agaisse et al., 1994. Expression in Bacillus subtilis of the Bacillus thuringiensis cryIIIA toxin gene is not dependent on a sporulation-specific sigma factor and is increased in a spo0A mutant. J. Bacteriol., 176(15):4734-4741.
Agaisse et al., 1994. Structural and functional analysis of the promoter region involved in full expression of the cryIIIA toxin gene of Bacillus thuringiensis. Mol. Microbiol., 13(1):97-107.
Ashikaga et al. (2000) "Natural genetic competence in Bacillus subtilis natto OK2," J Bacteriol. 182(9):2411-5.
Battcock, Fao, "Fermented Fruits and Vegetables: A Global Perspective", Agricultural Services Bulletin No. 134, 1998, 16 pages.
Baum et al. (1995) "Regulation of insecticidal crystal protein production in Bacillus thuringiensis," Mol. Microbiol. 18:1-12.
Beasley et al. (2004) "Nisin-producing Lactococcus lactis strains isolated from human milk," Appl Environ Microbiol. 70(8):5051-3.

(Continued)

*Primary Examiner* — Albert M Navarro
(74) *Attorney, Agent, or Firm* — LATHROP GPM LLP; James H. Velema, Esq.; Judith L. Stone-Hulslander, Esq.

(57) ABSTRACT

Compositions and methods for treating or reducing the severity of occurrence of a parasitic worm or helminth infection in a subject are described. The methods include administering to the subject a therapeutically effective amount of a composition comprising isolated native, bioactive nematicidal crystals formed from a single type of nematicidal crystal protein. The isolated native, bioactive nematicidal crystals are substantially free of any bacterial spores or host bacterial proteins, other than nematicidal crystal protein in the form of a crystal. Methods for making isolated native, bioactive nematicidal crystals are also described. The crystal proteins may be full length, truncated, variant, or sub-variant Cry proteins. Examples of crystal proteins include Cry5B, Cry21, Cry14A, Cry6A, and Cry13A.

33 Claims, 23 Drawing Sheets
Specification includes a Sequence Listing.

(56) References Cited

OTHER PUBLICATIONS

Bermúdez-Humarán et al., "Lactococci and lactobacillin as mucosal delivery vectors for therapeutic proteins and DNA vaccines", Microbial Cell Factories, 2011, pp. 1-10.
Berrelli et al. (Nov. 16, 2012) "Interactions between parasites and microbial communities in the human gut," Front Cell Infect Microbiol. 2:141. pp. 1-6.
Bethony et al. (2006) "Soil-transmitted helminth infections: ascariasis, trichuriasis, and hookworm," Lancet 367:1521-1532.
Betz et al. (2000) "Safety and advantages of Bacillus thuringiensis-protected plants to control insect pests," Regul. Toxicol. Pharmacol. 32(2):156-73.
Beveridge, "Cellular Responses of Bacillus subtilis and *Escherichia coli* to the Gram Stain", Journal of Bacteriology 1983, 156: 846-858.
Bischof et al. (2006) "Assays for toxicity studies in C. elegans with Bt crystal proteins," Methods Mol. Biol. 351:139-154.
Boontawan et al., 2005, Mass transfer of terpenes through a silicone rubber membrane in a liquid-liquid contacting system. Biotechnol. Prog., 21:1680-1687.
Braat et al. (2006) "A phase I trial with transgenic bacteria expressing interleukin-10 in Crohn's disease," Clin. Gastroenterol. Hepatol. 4:754-759.
Brans et al. (2004) "New integrative method to generate Bacillus subtilis recombinant strains free of selection markers," Appl. Environ. Microbiol. 70:7241-7250.
Brooker et al. (2008) "Hookworm-related anaemia among pregnant women: a systematic review," PLoS Negl. Trop. Dis. 2:e291. pp. 1-9.
Buasri et al. (Jan. 20, 2012) "Large crystal toxin formation in chromosomally engineered *Bacillus thuringiensis* subsp. *aizawai* due to GE accumulation," Appl. Environ. Microbiol. 78:1682-1691.
Cannon (1996) "Bacillus thuringiensis use in agriculture: a 30 molecular perspective," Biol. Rep. 71:561-636.
Capello et al., "A Purified Bacillus Thuringiensis Crystal Protein with Therapeutic Activity Against the Hookworm Parasite Ancylostoma Ceylanicum", Proceedings of the National Academy of Science, Oct. 10, 2006, vol. 103, No. 41, pp. 15154-15159.
Casula et al. (2002) "Bacillus probiotics: spore germination in the gastrointestinal tract," Appl. Environ. Microbiol. 68:23442352.
Chan et al., Thompson IP, 2013, Resolving the mechanism of bacterial inhibition by plant secondary metabolites employing a combination of whole-cell biosensor. J. Microbiol. Methods, 9 Pages.
Coêlho et al., "Probiotic Therapy: A Promising Strategy for the Control of Canine Hookworm", Journal of Parasitology Research, 2013, 6 pages.
Conlan et al. (Apr. 2012) "Soil-transmitted helminthiasis in Laos: a community-wide cross-sectional study of humans and dogs in a mass drug administration environment," Am. J. Trop. Med. Hyg. 86:624-634.
Crickmore et al. (1998) "Revision of the Nomenclature for the Bacillus thuringiensis Pesticidal Crystal Proteins," Microbiology and Molecular Biology Reviews. 62(3):807-813.
Cutting (2011) "Bacillus probiotics," Food Microbiol. 28:214220.
D'Arienzo et al. (2006) "Bacillus subtilis spores reduce susceptibility to Citrobacter rodentium-mediated enteropathy in a mouse model," Res. Microbiol. 157:891-897.
De Maagd et al., "How Baccillus thuringiensis has evolved specific toxins to colonize the insect world", Trends in Genetics 17(4): 193-199, Apr. 2001.
Dubnau et al. (1971) "Fate of transforming DNA following uptake by competent Bacillus subtilis. I. Formation and properties of the donor-recipient complex," J. Mol. Biol. 56:209-221.
Duc et al. (2003) "Bacterial spores as vaccine vehicles," Infect. Immun. 71:2810-2818.
Duc et al. (2004) "Characterization of Bacillus probiotics available for human use," Appl. Environ. Microbiol. 70(4):2161-2171.
Durmaz et al., (Dec. 18, 2015), "Intracellular and Extracellular Expression of Bacillus thuringiensis Crystal Protein Cry5B in Lactococcus lactis for Use as an Anthelminthic", Applied and Environmental Microbiology, vol. 82, No. 4, pp. 1286-1294.
El-Bendary (2006) Bacillus thuringiensis and Bacillus sphaericus biopesticides production, J. Basic Microbiol. 46:158-170.
Entomological Society of America (ESA), Is BT Safe for Human to Eat?, May 1, 2018, pp. 1-3.
Extended European Search Report for European Patent Application No. 18805734.3, mailed Mar. 31, 2021.
Ferrer-Miralles, "Bacterial cell factories for recombinant protein production; expanding the catalogue", Microbial Cell Factories, 2013, 12:113.
Fujiwara et al., 2006. Comparative immunology of human and animal models of hookworm infection. Parasite Immunol., 28:285-293.
Ge et al. (1990) "Hyperexpression of a Bacillus thuringiensis delta-endotoxin gene in *Escherichia coli*: properties of the product," Gene, 93:49-54.
Geary et al. (2010) Unresolved issues in anthelmintic pharmacology for helminthiases of 30 humans, Int. J. Parasitol. 40:1-13.
Geertsma et al. (2007) "High-throughput cloning and expression in recalcitrant bacteria," Nat Methods. 4:705-707.
Genbank Database [Online] (Sep. 23, 2008) "truncated Cry5B [synthetic construct]," Accession No. ACI01644. National Center for Biotechnology Information. Accessible on the Internet at URL: https://www.ncbi.nlm.nih.gov/protein/ACI01644. [Last Accessed May 4, 2017].
Goh et al. (2009) "Development and application of a upp-based counterselective gene replacement system for the study of the S-layer protein SlpX of Lactobacillus acidophilus NCFM," Appl. Environ. Microbiol. 75(10):3093-105.
Griffitts et al. (2001) "Bt toxin resistance from loss of a putative carbohydrate-modifying enzyme," Science. 293(5531):860-4.
Griffitts et al. (2005) "Glycolipids as receptors for Bacillus thuringiensis crystal toxin," Science. 307:922-925.
Griffitts et al. (2005) "Many roads to resistance: how invertebrates adapt to Bt toxins," Bioessays. 27:614-624.
Hall et al. (2008) "A review and metaanalysis of the impact of intestinal worms on child growth and nutrition," Matern. Child Nutr. 4(Suppl 1):118-236.
Hoa et al. (2000) "Characterization of *Bacillus* species used for oral bacteriotherapy and bacterioprophylaxis of gastrointestinal disorders," Appl. Environ. Microbiol. 66:5241-5247.
Hoa et al. (2001) "Fate and dissemination of Bacillus subtilis spores in a murine model," Appl. Environ. Microbiol. 67:3819-3823.
Hoang et al. (2008) "Recombinant Bacillus subtilis expressing the Clostridium perfringens alpha toxoid is a candidate orally delivered vaccine against necrotic enteritis," Infect. Immun. 76:5257-5265.
Holck et al. (1992) "Cloning, sequencing and expression of the gene encoding the cell-envelope-associated proteinase from *Lactobacillus paracasei* subsp. *paracasei* NCDO 151," J. Gen. Microbiol. 138(7):1353-64.
Holden-Dye et al. (2007) "Anthelmintic drugs," WormBook. 2:1-13.
Hong et al. (2008) "The safety of Bacillus subtilis and Bacillus indicus as food probiotics," J. Appl. Microbiol. 105:510-520.
Hotez PJ. 2008. Forgotten people, forgotten diseases: the neglected tropical diseases and their impact on global health and development. ASM Press, Washington, DC.
Hu et al. (2009) "The new anthelmintic tribendimidine is an L-type (levamisole and pyrantel) nicotinic acetylcholine receptor agonist," PLoS Negl. Trop. Dis. 3:e499. pp. 1-9.
Hu et al. (2010) "Bacillus thuringiensis Cry5B protein is highly efficacious as a single-dose therapy against an intestinal roundworm infection in mice," PLoS Negl. Trop. Dis. 4:e614. pp. 1-7.
Hu et al. (2012) "Promise of Bacillus thuringiensis crystal proteins as anthelmintics," In; Parasitic Helminths: Targets, Screens, Drugs and Vaccines. Ed.: Caffery. Wiley-VCH Verlag Gmh & Co. Weinheim, Germany. pp. 267-281.
Hu et al. (Jul. 8, 2013) "Bacillus subtilis strain engineered for treatment of soil-transmitted helminth diseases," Appl. Environ. Microbiol. 79(18):5527-5532.

(56) References Cited

OTHER PUBLICATIONS

Hu et al. (Nov. 8, 2012) "Mechanistic and single-dose in vivo therapeutic studies of Cry5B anthelmintic action against hookworms," PLoS Negl. Trop. Dis. 6:e1900. pp. 1-8.
Hu et al., "Discovery of a highly synergistic anthelmintic combination that shows mutual hypersusceptibility" PNAS, vol. 107, No. 13, pp. 5955-5960, Mar. 30, 2010.
Hu et al., 2013, An extensive comparison of the effect of anthelmintic classes on diverse nematodes. PLoS One, 8(7):e70702, 12 pages.
Humphries et al. (2011) "Epidemiology of hookworm infection in Kintampo North Municipality, Ghana: patterns of malaria coinfection, anemia, and albendazole treatment failure," Am. J. Trop. Med. Hyg. 84:792800.
Iatsenko, "Molecular Mechanisms of Caenorhabditis elegans—Bacillus Interactions", Dissertation, der Eberhard Karls Universitht Tubingen, Jun. 23, 2014.
International Search Report and Written Opinion for PCT International Application No. PCT/US2017/013436, dated May 24, 2017.
International Search Report and Written Opinion for PCT International Patent Application No. PCT/US2018/033962, dated Oct. 3, 2018.
International Search Report with Written Opinion for PCT International Patent Application No. PCT/US2015/038881, dated Oct. 14, 2015.
Keiser et al. (2008) "Efficacy of current drugs against soil-transmitted helminth infections: systematic review and meta-analysis," JAMA 299:1937-48.
Keiser et al. (2010) "The drugs we have and the drugs we need against major helminth infections," Adv. Parasitol. 73:197-230.
Kho et al. (2011) "The pore-forming protein Cry5B elicits the pathogenicity of Bacillus sp. against Caenorhabditis elegans," PLoS One 6:e29122. pp. 1-9.
Knopp et al. (Apr. 20, 2012) "Nematode infections: soil-transmitted helminths and trichinella," Infect. Dis. Clin. North Am. 26:341-358.
Krings U, Berger RG. 1998. Biotechnological production of Øavours and fragrances. Appl. Microbiol. Biotechnol., 49:1-8.
Kunle et al., "Antimicrobial activity of various extracts and carvacrol from *Lippia multiflora* leaf extract", Phytomedicine, vol. 10, pp. 59-61, 2003.
Kurek et al., "How composition and process parameters affect volatile active compounds in biopolymer films," Carbohydrate Polymers, vol. 88, pp. 646-656, 2012.
La Ragione et al. (2001) "Bacillus subtilis spores competitively exclude *Escherichia coli* O78:K80 in poultry," Vet. Microbiol. 79:133-142.
La Ragione et al. (2003) "Competitive exclusion by Bacillus subtilis spores of *Salmonella enterica* serotype Enteritidis and Clostridium perfringens in young chickens," Vet. Microbiol. 94:245-256.
Law et al. (1995) "A system to generate chromosomal mutations in Lactococcus lactis which allows fast analysis of targeted genes," J. Bacteriol. 177:7011-7018.
Lee et al., 2011, Utility of capsule endoscopy for evaluating anthelmintic efficacy in fully conscious dogs. Int. J. Parasitol., 41:1377-1383.
Lee et al., 2015, Determination of anthelmintic efficacy against Toxocara canis in dogs by use of capsule endoscopy. Vet. Parasitol., 212:227-231.
Lereclus et al., "Overproduction of Encapsulated Insecticidal Crystal Proteins in a Bacillus Thuringiensis Spo0A Mutant", Nature Biotechnology, Jan. 1, 1995, vol. 13, pp. 67-70.
Lereclus et al., "Transformation and Expression of a Cloned δ-Endotoxin Gene in Bacillus Thuringiensis", FEMS Microbiology Letters, Jul. 1989, vol. 60, Issue 2, pp. 211-217.
Li et al. (2008) "Expression of Cry5B protein from Bacillus thuringiensis in plant roots confers resistance to root-knot nematode," Biol. Control. 47(1):97-102.
Los et al. (2011) "RAB-5- and RAB-11-dependent vesicle-trafficking pathways are required for plasma membrane repair after attack by bacterial poreforming toxin," Cell Host Microbe 9:147-157.

Maagd et al. (2001) "How Bacillus thuringiensis has evolved specific toxins to colonize the insect world." Trends in Genetics. 17(4):193-99.
Malvar et al., "Tn5401 Disruption of the spoOF Gene Identified by Direct Chromosomal Sequencing, Results in CryIIIIA Overproduction in Bacillus thuringiensis", J Bacteriol. 176, 4750-4753, 1994.
Marroquin et al. (2000) "Bacillus thuringiensis (Bt) toxin susceptibility and isolation of resistance mutants in the nematode Caenorhabditis elegans," Genetics. 155:1693-1699.
McClemens et al. (Jun. 2013) "Lactobacillus rhamnosus Ingestion Promotes Innate Host Defense in an Enteric Parasitic Infection," Clinical and Vaccine Immunology. 20(6):818-826.
Mohamadzadeh et al. (2009) "Dendritic cell targeting of Bacillus anthracis protective antigen expressed by Lactobacillus acidophilus protects mice from lethal challenge," Pproc. Natl. Acad. Sci. USA. 106: 4331-4336.
Moran et al. (2009) G-finder Report: Neglected Disease Research and Development: New Times, New Trends. Global Fund of Innovation for Neglected Diseases, 106 Pages.
Mounsef et al., "A simple method for the separation of Bacillus thuringiensis spores and crystals", Journal of Microbiological Methods, vol. 107, pp. 147-149, 2014.
National Research Council. 1996. Guide for the care and use of laboratory animals. National Academies Press, Washington, DC.
NIH, "RecName: Full=Pesticidal crystal protein Cry5Ba; AltName: Full=140 kDa crystal protein; AltName: Full=Crystaline entomocidal protoxin; AltName: Full=Insecticidal delta-endotoxin CryVB(a)", UniProtKB/Swiss-Prot: Q45712.1, created Dec. 1, 2000.
Norton et al. (1996) "Factors affecting the immunogenicity of tetanus toxin fragment C expressed in Lactococcus lactis," FEMS Immunol. Med. Microbiol. 14:167-177.
Oddone et al. (2009) "Incorporation of nisI-mediated nisin immunity improves vector-based nisin-controlled gene expression in lactic acid bacteria," Plasmid. 61:151-158.
Partial European Search Report received for European Patent Application No. 18805734.3, mailed on Dec. 1, 2020.
Peltzer et al., "Migration of carvacrol as a natural antioxidant in high-density polyethylene for active packaging," Food Additives and Contaminants, vol. 26, No. 6, pp. 938-946, 2009.
Peng et al., "A δ-endotoxin encoded in Pseudomonas fluorescens displays a high degree of insecticidal activity", App. Microbiol Biotech, 63: 300-306, 2003.
Permpoonpattana et al. (2011) "Immunization with Bacillus spores expressing toxin A peptide repeats protects against infection with Clostridium difficile strains producing toxins A and B," Infect. Immun. 79:22952302.
Phan et al. (2006) "Novel plasmid-based expression vectors for intra- and extracellular production of recombinant proteins in Bacillus subtilis," Protein Expr. Purif. 46(2):189-95.
Pusch et al. (2005) "Bioengineering Lactic Acid Bacteria to Secrete the HIV-1 Virucide Cyanovirin," J. Acquir. Immune. Defic. Syndr. 40(5):512-20.
Pusch et al. (2006) "An anti-HIV microbicide engineered in commensal bacteria: secretion of HIV-1 fusion inhibitors by lactobacilli," AIDS. 20:1917-1922.
Roh et al. (2007) "Bacillus thuringiensis as a specific, safe, and effective tool for insect pest control," J. Microbiol. Biotechnol. 17(4):547-59.
Romero et al. (2006) "Transformation of undomesticated strains of Bacillus subtilis by protoplast electroporation," J. Microbiol. Meth. 66(3):556-9.
Rowley et al., "Solvent extraction of penicillin," Journal of the Society of Chemical Industry, vol. 65, No. 8, pp. 237-240, 1946.
Rudd A. de Maagd et al. (2001) "How Bacillus thuringiensis has evolved specific toxins to colonize the insect world," Trends in Genetics, 17(4):193-199.
Russell et al. (2001) "Identification and cloning of gusA, encoding a new beta-glucuronidase from Lactobacillus gasseri ADH," Appl. Environ. Microbiol. 67(3):1253-61.
Sandman et al., "Genetic Analysis of Bacillus subtilis spo Mutations Generated by Tn917-Mediated Insertional Mutagenesis", Genetics, vol. 117, pp. 603-617, Dec. 1987.

(56) References Cited

OTHER PUBLICATIONS

Schallmey et al. (2004) "Developments in the use of *Bacillus species* for industrial production," Can. J. Microbiol. 50:1-17.
Schnepf et al., "Bacillus thuringiensis and Its Pesticidal Crystal Proteins", Microbiology and Molecular Biology Reviews, vol. 62, No. 3, pp. 775-806, Sep. 1998.
Schroeder et al. (2006) "Preventive effects of the probiotic *Escherichia coli* strain Nissle 1917 on acute secretory diarrhea in a pig model of intestinal infection," Dig. Dis. Sci. 51:724-731.
Shao et al. (2009) "Surface display of heterologous proteins in Bacillus thuringiensis using a peptidoglycan hydrolase anchor," Microb. Cell Fact. 8:48. pp. 1-17.
Shevchenko et al. (1996) "Mass spectrometric sequencing of proteins silver-stained polyacrylamide gels," Anal. Chem. 68:850-858.
Shkoporov et al. (2008) "Production of human basic fibroblast growth factor (FGF-2) in Bifidobacterium breve using a series of novel expression/secretion vectors," Biotechnol. Lett. 30:1983-1988.
Sierro et al. (2008) "DBTBS: a database of transcriptional regulation in Bacillus subtilis containing upstream intergenic conservation information," Nucleic Acids Res. 36:D93-D96.
Silvaggi et al., "Unmasking Novel Sporulation Genes in Bacillus subtillus", J Bacteriol. vol. 186, No. 23, pp. 8089-8095, Dec. 2004.
Sivropoulou et al., "Antimicrobial and Cytotoxic Activities of Origanum Essential Oils," Journal of Agricultural and Food Chemistry, vol. 44, No. 5, pp. 1202-1205, 1996.
Song et al. (Mar. 22, 2012) "Killed Bacillus subtilis spores as a mucosal adjuvant for an H5N1 vaccine," Vaccine 30:3266-3277.
Soukhathammavong et al. (Jan. 3, 2012) Low efficacy of single-dose albendazole and mebendazole against hookworm and effect on concomitant helminth infection in Lao PDR, PLoS Negl. Trop. Dis. 6(1):e1417. pp. 1-8.
Steidler et al. (2000) "Treatment of murine colitis by Lactococcus lactis secreting interleukin-10," Science. 289:1352-1355.
Steidler et al., "Biological containment of genetically modified Lactococcus lactis for intestinal delivery of human interleukin 10", Nat Biotechnol 21: 785-789, 2003.
Stepek et al. 2007. Anthelmintic action of plant cysteine proteinases against the rodent stomach nematode, Protospirura muricola, in vitro and in vivo. Parasitology, 134:103-112.
Stothard et al. (2009) "A spot-check of the efficacies of albendazole or levamisole, against soil-transmitted helminthiases in young Ungujan children, reveals low frequencies of cure," Ann. Trop. Med. Parasitol. 103:357-360.
Tchuenté (2011) "Control of soil-transmitted 5 helminths in sub-Saharan Africa: diagnosis, drug efficacy concerns and challenges," Acta Trop. 120(Suppl 1):S4-S11.
Tritten et al. (2011) "In vitro and in vivo efficacy of monepantel (AAD 1566) against laboratory models of human intestinal nematode infections," PLoS Negl. Trop. Dis. 5:e1457. pp. 1-7.
Tritten et al. (Dec. 24, 2011) "In vitro and in vivo efficacy of tribendimidine and its metabolites alone and in combination against the hookworms *Heligmosomoides bakeri* and *Ancylostoma ceylanicum*," Acta Trop. 122:101-107.
Urban et al. (Jun. 20, 2013) "Bacillus thuringiensis-derived Cry5B has potent anthelmintic activity against Ascaris suum," PLoS Negl Trop Dis. 7(6):e2263. pp. 1-7.
Valadares de Amorim, et al., "Identification of *Bacillus thuringiensis* subsp. *kurstaki* Strain HD1-Like Bacteria from Environmental and Human Samples after Aerial Spraying of Victoria, British Columbia, Canada, with Foray 48B", Applied And Environmental Microbiology, Mar. 2001, 67(3): 1035-1043.
Waeytens et al. (2008) "Paracellular entry of interleukin-10 producing Lactococcus lactis in inflamed intestinal mucosa in mice," Inflamm. Bowel Dis. 14(4):471-9.
Walker et al. (1996) "Electrotransformation of lactobacillus acidophilus group A1," FEMS Microbiol. Lett. 138(2-3):233-7.
Wang et al. (Aug. 3, 2012) "Improvement of crystal solubility and increasing toxicity against Caenorhabditis elegans by asparagine substitution in block 3 of Bacillus thuringiensis crystal protein Cry5Ba," Appl. Environ. Microbiol. 78:7197-7204.
Wei et al. (2003) "Bacillus thuringiensis crystal proteins that target nematodes," Proc Natl. Acad. Sci. USA. 100(5):2760-5.
Wells et al. (2008) "Mucosal delivery of therapeutic and prophylactic molecules using lactic acid bacteria," Nat Rev Microbiol. 6(5):349-62.
Yang et al. (1996) "Cloning and expression of full-length delta-endotoxin cryIA(c) gene in three kinds of prokaryotic systems using shuttle vector pHT3101," Wei Sheng Wu Xue Bao. 36:173-180.—English Abstract Only.
Yoshisue et al., "Identification of a promoter for the crystal protein-encoding gene cryIVB from *Bacillus thuringiensis* subsp. *Israelensis*," Gene, Dec. 31, 1993, 137(2): 247-251.
Youngman et al. (1984) "Construction of a cloning site near one end of Tn917 into which foreign DNA may be inserted without affecting transposition in Bacillus subtilis or expression of the transposonborne erm gene," Plasmid 12:1-9.
Zhang et al., "Evaluation of alginate—whey protein microcapsules for intestinal delivery of lipophilic compounds in pigs," J Sci Food Agric, vol. 96, pp. 2674-2681, 2016.
U.S. Appl. No. 15/321,642 2017/0348362 U.S. Pat. No. 10,940,170, filed Dec. 22, 2016 Dec. 7, 2017 Mar. 9, 2021, Raffi Van Aroian, Anthelmintic Probiotic Compositions and Methods.
U.S. Appl. No. 17/160,030 2021/0268045, filed Jan. 27, 2021 Sep. 2, 2021, Raffi Van Aroian, Anthelmintic Probiotic Compositions and Methods.
U.S. Appl. No. 16/067,109 2019/0015474 U.S. Pat. No. 11,484,568, filed Jun. 28, 2018 Jan. 17, 2019 Jun. 28, 2018, Raffi Van Aroian, Anthelmintic Compositions and Methods.
U.S. Appl. No. 17/934,848 2023/0128953, filed Sep. 23, 2022 Apr. 27, 2023, Raffi Van Aroian, Anthelmintic Compositions and Methods.
U.S. Appl. No. 16/607,677 2020/0188452 U.S. Pat. No. 11,844,815, filed Oct. 23, 2019 Jun. 18, 2020 Dec. 19, 2023, Raffi Van Aroian, Purified Anthelmintic Compositions and Related Methods.
U.S. Appl. No. 17/729,785 2022/0354905 U.S. Pat. No. 11,826,389, filed Apr. 26, 2022 Nov. 10, 2022 Nov. 28, 2023, Raffi Van Aroian, Purified Anthelmintic Compositions and Related Methods.
Hu et al., "Bacterial pore-forming proteins as anthelmintics", Invert Neurosci., Jun. 2012, 12(1): 37-41.
Hui et al., "The structure and glycolipid-binding properties of the nematicidal protein Cry5B", Biochemistry, Dec. 11, 2012, 51(49): 9911-9921.
Georghiou, "An investigation into the anthelmintic properties and syergistic potential of Cry5B", Thesis for Master of Science degree in Biology at the University of California, San Diego, 2010.

Cry5Ba1

| | | | | | | |
|---|---|---|---|---|---|---|
| 1 | MATINELYPV | PYNVLAHPIK | EVDDPYSWSN | LLKGIQEGWE | EWGKTGQKKL | FEDHLTIAWN |
| 61 | LYKTGKLDYE | ALTKASISLI | GFIPGAEAAV | PFINMEVDFV | WPKLFGANTE | GKDQQLFNAI |
| 121 | MDAVNKMVDN | KFLSYNLSTL | NKTIEGIQGN | LGLFQNAIQV | AICQGSTPER | VNFDQNCTPC |
| 181 | NPNQPCKDDL | DRVASRFDTA | NSQFTQHLPE | FKNPWSDENS | TQEFKRTSVE | LTLPMYTTVA |
| 141 | TLHLLLYEGY | IEFMTKWNFH | NEQYLNNLKV | ELQQLIHSYS | ETVRTSFLQF | LPTLNNRSKS |
| 301 | SVNAYNRYVR | NMTVNCLDIA | ATWPTFDTHN | YHQGGKLDLT | RIILSDTAGP | IEEYTTGDKT |
| 361 | SGPEHSNITP | NNILDTPSPT | YQHSFVSVDS | IVYSRKELQQ | LDIATYSTNN | SNNCHPYGLR |
| 421 | LSYTDGSRYD | YGDNQPDFTT | SNNNYCHNSY | TAPITLVNAR | HLYNAKGSLQ | NVESLVVSTV |
| 481 | NGGSGSCICD | AWINYLRPPQ | TAKNESFPDQ | KDNVLYPITE | TVNKGTGGNL | GVISAYVPME |
| 541 | LVPENVIGDV | NADTKLPLTQ | LKGFPFEKYG | SEYNNRGISL | VREWINGNNA | VKLSNSQSVG |
| 601 | IQITNQTEQK | YEIRCRYASK | GDNNVYFNVD | LSENPFRNSI | SFGSTESSVV | GVQGENGKYI |
| 661 | LKSITTVEIP | AGSFYVHITN | QGSSDLFLDF | IEFVPKIQFQ | FCDNNNLHCD | CNNPVDTDCT |
| 721 | FCCVCTSLTD | CDCNNPRGLD | CTLCCQVENQ | LPSFVTLTDL | QNITTQVNAL | VASSEHDTLA |
| 781 | TDVSDYEIEE | VVLKVDALSG | EVFGKEKKAL | RKLVNHTKRL | SKARNLLIGG | NFDNLDAWYR |
| 841 | GRNVVNVSDH | ELFKSDHYLL | PPPTLYSSYM | FQKVEESKLK | ANTRYSVSGF | IAHAEDLEIV |
| 901 | VSEYGQEVKK | VVQVPYGEAF | PLTSRGAICC | PPRSTSNGKP | ADPHEFSYSI | DVGTLDVEAN |
| 961 | PGIELGLRIV | ERTGMARYSN | LEIREDPPLK | KNELRNVQRA | ARNWRSAYDQ | ERAEVTALIQ |
| 1021 | PVLNQINALY | ENEDWNGAIR | SGVSYHDLEA | IVLPTLPKLN | HWFMSDMLGE | QGSILAQFQE |
| 1081 | ALDRAYTQLE | ESTILHNGHF | TTDAANWTIE | GDAHHAILED | GRRVLRLPDW | SSSVSQTIEI |
| 1141 | ENFDPDKEYQ | LVFHAQGEGT | VSLQHGEEGE | YVETHPHKSA | NFTTSHRQGL | TFETNKVTVE |
| 1201 | ITSEDGEFLV | DHIALVEAPL | PTDDQSSDGN | TFSNTNSNTS | MNNNQ | |

*Fig. 2*

Cry13Aa1

```
  1  MTCQLQAQPL IPYNVLAGYP TSNTGSPIGN AGNQFDQFEQ TVKELKEAWE AFQKNGSFSL
 61  AALEKGFDAA IGGGSFDYLG LVQAGLGLVG TLGAAIPGVS VAVPLISMLV GVFWPKGTNN
121  QENLITVIDK EVQRILDEKL SDQLIKKINA DLNAFTDLVT RLEEVIIDAT FENHKPVLQV
181  SKSNYMKVDS AYFSTGGILT LGMSDFLTDT YSKLTFPLYV LGATMKLSAY HSYIQFGNTW
241  LNKVYDLSSD EGKTMSQALA RAKQHMRQDI AFYTSQALNM FTGNLPSLSS NKYAINDYNV
301  YTRAMVLNGL DIVATWPTLY PDDYSSQIKL EKTRVIFSDM VGQSESRDGS VTIKNIFDNT
361  DSHQHGSIGL NSISYFPDEL QKAQLRMYDY NHKPYCTDCF CWPYGVILNY NKNTFRYGDN
421  DPGLSGDVQL PAPMSVVNAQ TQTAQYTDGE NINTDTGRSW LCTLRGYCTT NCFPGRGCYN
481  NSTGYGESCN QSLPGQKIHA LYPFTQTNVL GQSGKLGLLA SHIPYDLSPN NTIGDKDTDS
541  TNIVAKGIPV EKGYASSGQK VEIIREWING ANVVQLSPGQ SWGMDFTNST GGQYMVRCRY
601  ASTNDTPIFF NLVYDGGSNP IYNQMTFPAT KETPAHDSVD NEILGIKGIN GNYSLMNVKD
661  SVELPSGKFH VFFTNNGSSA IYLDRLEFVP LDQPAAPTQS TQPINYPITS RLPHRSGEPP
721  AIIWEKSGNV RGNQLTISAQ GVPENSQIYL SVGGDRQILD RSNGFKLVNY SPTYSFTNIQ
781  ASSSNLVDIT SGTITGQVQV SNL
```

Fig. 3

Cry14Aa1

1 MDCNLQSQQN IPYNVLAIPV SNVNALVDTA GDLKKAWEEF QKTGSFSLTA LQQGFSASQG
61 GAFNYLTLLQ SGISLAGSFV PGGTFVAPIV NMVIGWLWPH ENKTADTENL IKLIDEEIQK
121 QLNKALLDQD RNNWTSFLES IFDTSATVSN ADIDAQWSGT VDTTNRQQKT PTTSDYLNVV
181 GKFDSADSSI ITNENQIMNG NFDVAAAPYF VDGATLRLSL YQSYIKFCNS WIDAVGFSTN
141 DANTQKANLA RTKLTMRSTI NEYTQRVMKV FKDSKNMPTI GTNKFSVDAY NVYVKGMTLN
301 VLDMVAIWSS LYPNDYTSQT AIEQTRVTFS NMVGQEEGTD GTLKIYNTFD SLSYQHSLIP
361 NNNVNLISYY TDELQNLELA VYTPKGGSGY AYPYGFILNY ANSNYKYGDN DPTGKPLNKQ
421 DGPIQQINAA TQNSKYLDGE TINGIGASLP GYCTTGSSAT EQPFSCTGTA NSYKASCNPS
481 DTNQKINALY AFTQTNVKGS TGKLGVLASL VPYDLNPKNV FGELDSDTNN VILKGIPAEK
541 GYFPNNARPT VVKEWINGAS AVPFYSGNTL FMTATNLTAT QYKIRIRYAN PNSDTQISVL
601 ITQNGSQISN SNLTLYSTTD SSMSSNLPQN VYVTGENGNY TLLDLYSTTN VLSTGDITLK
661 LTGGNQKIFI DRIEFIPTMP VPAPTNNTNN NNGDNGNNNP PHHGCAIAGT QQLCSGPPKF
721 EQVSDLEKIT TQVYMLFKSS SYEELAIKVS SYQINQVALK VMALSDEKFC EEKRLLRKLV
781 NKANQLLEAR NLLVGGNFET TQNWVLGTNA YDNYDSFLFN GNYLSLQPAS GFFTSYAYQK
841 IDESTLKPYT RYKVSGFIGQ SNQVELIISR YGKEIDKILN VPYAGPLPIT ADASITCCAP
901 EIDQCDGGQS DSHFFNYSID VGALHPELNP GDEIGLKIVQ SNGYISISNL EIIEERPLTE
961 MEIQAVNRKD QKWKRELLLE CASVSELLQP IDNQIDSLFK DANWYNDILP HVTYQTLKNI
1021 IVPDLPKLKH WFIDHLPGEY HEIEQKMKEA LKHAFTQLDE KNLIHNGHFA TNLIDWQVEG
1081 DAFMKVLENN ALALQLSNWD SSVSQSIDIL EFDEDKAYKL RVYAQGSGTI QFGNCEDEAI
1141 QFNTNSFVYK EKIIYFDSPS INLHIQSEGS EFVVSSIDLV ELSDDE

*Fig. 4*

Cry14Aa1

MTNPTILYPSYHNVLAHPIRLDSFFDPFVETFKDLKGAWEEFGKTGYMDPLKQHLQIAWD
TSQNGTVDYLALTKASISLIGLIPGADAVVPFINMFVDFIFPKLFGRGSQQNAQAQFFEL
IIEKVKELVDEDFRNFTLNNLLNYLDGMQTALSHFQNDVQIAICQGEQPGLMLDQTPTAC
TPTTDHLISVRESFKDARTTIETALPHFKNPNLSTNDNTPDFNSDTVLLTLPMYTTGATL
NLILHQGYIQFAERWKSVNYDESFINQTKVDLQRRIQDYSTTVSTTFEKFKPTLNPSNKE
SVNKYNRYVRSMTLQSLDIAATWPTLDNVNYPSNVDIQLDQTRLVFSDVAGPWEGNDNIT
SNIIDVLTPINTGIGFQESSDLRKFTYPRIELQSMQFHGQYVNSKSVEHCYSDGLKLNYK
NKTITAGVSNIDESNQNNKHNYGPVINSPITDINVNSQNSQYLDLNSVMVNGGQKVTGCS
PLSSNGNSNNAALPNQKINVIYSVQSNDKPEKHADTYRKWGYMSSHIPYDLVPENVIGDI
DPDTKQPSLLLKGFPAEKGYGDSIAYVSEPLNGANAVKLTSYQVLQMEVTNQTTQKYRIR
IRYATGGDTAASIWFHIIGPSGNDLTNEGHNFSSVSSRNKMFVQGNNGKYVLNILTDSIE
LPSGQQTILIQNTNSQDLFLDRIEFISLPSTSTPTSTNFVEPESLEKIINQVNQLFSSSS
QTELAHTVSDYKIDQVVLKVNALSDDVFGVEKKALRKLVNQAKQLSKARNVLVGGNFEKG
HEWALSREATMVANHELFKGDHLLLPPPTLYPSYAYQKIDESKLKSNTRYTVSGFIAQSE
HLEVVVSRYGKEVHDMLDIPYEEALPISSDESPNCCKPAACQCSSCDGSQSDSHFFSYSI
DVGSLQSDVNLGIEFGLRIAKPNGFAKISNLEIKEDRPLTEKEIKKVQRKEQKWKKAFNQ
EQAEVATTLQPTLDQINALYQNEDWNGSVHPASDYQHLSAVVVPTLPKQRHWFMEGREGE
HVVLTQQFQQALDRAFQQIEEQNLTHNGNLANGLTDWTVTGDAQLTIFDEDPVLELAHWD
ASISQTIEIMDFEGRHRIQTACTWKRQRNSYRSTWRKRLETMTFNTTSFTTQEQTFYFEG
DTVDVHVQSENNTFLIDSVELIEIIEE

*Fig. 5A*

Cry21Aa2
(98% identical to Cry21Aa1)

MTNPTILYPSYHNVLAHPIRLDSFFDPFVETFKDLKSAWEEFGKTGYMDPLKQHLQIAWD
TSQNGTVDYLALTKASISLIGLIPGADAVVPFINMFVDFIFPKLFGRGSQQNAQAQFFEL
IIEKVKELVDEDFRNFTLNNLLNYLDGMQTALSHFQNDVQIAICQGEQPGLMLDQTPTAC
TPTTDHLISVRESFKDARTTIETALPHFKNPNLSTNDNTPDFNSDTVLLTLPMYTTAATL
NLILHQGYIQFAERWKSVNYDESFINQTKVDLQRRIQDYSTTVSTTFEKFKPTLNPSNKE
SVNKYNRYVRSMTLQSLDIAATWPTLDNVNYPSNVDIQLDQTRLVFSDVAGPWEGNDNIT
SNIIDVLTPINTGIGFQESSDLRKFTYPRIELQSMQFHGQYVNSKSVEHCYSDGLKLNYK
NKTITAGVSNIDESNQNNKHNYGPVINSPITDINVNSQNSQYLDLNSVMVNGGQKVAGCS
PLSSNGNSNNAALPNQKINVIYSVQSNDKPEKHADTYRKWGYMSSHIPYDLVPENVIGDI
DPDTKQPSLLLKGFPAEKGYGDSIAYVSEPLNGANAVKLTSYQVLKMEVTNQTTQKYRIR
IRYATGGDTAASIWFHIIGPSGNDLTNEGHNFSSVSSRNKMFVQGNNGKYVLNILTDSIE
LPSGQQTILIQNTNSQDLFLDRIEFISLPSTSTPTSTNFVEPESLEKIINQVNQLFSSSS
QTELAHTVSDYKIDQVVLKVNALSDDVFGVEKKALRKLVNQAKQLSKARNVLVGGNFEKG
HEWALSREATMVANHELFKGDHLLLPPPTLYPSYAYQKIDESKLKSNTRYTVSGFIAQSE
HLEVVVSRYGKEVHDMLDIPYEEALPISSDESPNCCKPAACQCSSCDGSQSDSHFFSYSI
DVGSLQSDVNLGIEFGLRIAKPNGFAKISNLEIKEDRPLTEKEIKKVQRKEQKWKKAFNQ
EQAEVATTLQPTLDQINALYQNEDWNGSVHPHVTYQHLSAVVVPTLPKQRHWFMEDREGE
HVVLTQQFQQALDRAFQQIEEQNLIHNGNFANGLTDWTVTGDAQLSIFDEDPVLELAHWD
ASISQTIEIMDFEEDTEYKLRVRGKGKGTVTVQHGEEELETMTFNSTSFTTQEQTFYFEG
DTVDVHVQSENNTFLIDSVELIEIIEE

*Fig. 5B*

MIIDSKTTLPRHSLIHTIKLNSNKKYGPGDMTNGNQFIISKQEWATIGAYIQTGLGLPVNEQQLRTHVNL
SQDISIPSDFSQLYDVYCSDKTSAEWWNKNLYPLIKSANDIASYGFKVAGDPSIKKDGYFKKLQDELDN
IVDNNSDDDAIAKAIKDFKARCGILIKEAKQYEEAAKNIVTSLDQFLHGDQKKLEGVINIQKRLKEVQTA
LNQAHGESSPAHKELLEKVKNLKTTLERTIKAEQDLEKKVEYSFLLGPLLGFVVYEILENTAVQHIKNQI
DEIKEQLDSAQHDLDRDVKIIGMLNSINTDIDNLYSQGQEAIKVFQKLQGIWATIGAQIENLRTTSLQEV
QDSDDADEIQIELEDASDAWLVVAQEARDFTLNAYSTNSRQNLPINVISDSCNCSTTNMTSNQYSNPTTN
MTSNQYMISHEYTSLPNNFMLSRNSNLEYKCPENNFMIYWYNNSDWYNNSDWYNN

*Fig. 5C*

Legend
1. IBaCC homogenized (5 ul, 200 OD)
2. IBaCC homogenized sup (15 ul)
3. Water layer (15 ul)
4. NaCl wash (15 ul)
5. PBS wash (15 ul)
6. PCC oil wash final (5 ul, OD 312) large scale

PURIFIED ANTHELMINTIC COMPOSITIONS AND RELATED METHODS

RELATED APPLICATIONS

This application is a division of U.S. patent application Ser. No. 16/607,677, filed Oct. 23, 2019, which is a 35 U.S.C. § 371 filing of International Patent Application No. PCT/US2018/033962, filed May 22, 2018, which claims priority to U.S. Provisional Patent Application Ser. No. 62/510,081, filed May 23, 2017, the entire contents of which are incorporated herein by reference.

STATEMENT OF FEDERALLY SPONSORED RESEARCH

This invention was made with government support under Grant Nos. AI056189 awarded by the United States Department of Health and Human Services (HHS) National Institutes of Health (NIH), and NIFA 2016-67015-24861 awarded by the United States Department of Agriculture (USDA) National Institutes of Food and Agriculture (NIFA). The government has certain rights in this invention.

SEQUENCE LISTING

The instant application contains a Sequence Listing which has been submitted electronically in XML format and is hereby incorporated by reference in its entirety. Said XML file, created on Oct. 12, 2023, is named 746913_UM9-222USDIV2_ST26.xml and is 35,238 bytes in size.

BACKGROUND

Soil-transmitted helminthes (STHs) that parasitize the GI tract of humans infect 2.3 billion of the poorest peoples and >400,000,000 of the poorest children worldwide. Crystal (Cry) proteins made by the soil bacterium *Bacillus thuringiensis* (Bt) are candidate agents that provide safe and effective treatment of STHs. However, despite the established anthelmintic biological activity of Cry proteins, significant challenges remain with respect to effective delivery of intact, biologically active Cry proteins into the gastrointestinal (GI) tract of humans and animals for treating STHs. The cost and scalability of Cry protein expression and purification limits its application as a practical STH therapy in the developing world where treatments must be available at a very low cost (less than $1/dose) and in very large quantities to treat a large and poor patient population.

A cheap, simple, and scalable way to deliver Cry proteins is to express it in *B. thuringiensis*, which is ideally suited to express very high levels of Cry protein and which is already fermented cheaply on a massive scale for environmental release. However, production of high levels of Cry protein in Bt requires sporulation. Thus, the Cry protein compositions currently deployed into the environment are in the form of a "spore-crystal lysate" (SCL) that includes both the crystal protein and spores from the bacterium. Use of these SCL compositions in humans is problematic due to the presence of bacterial spores which can contain many of the enterotoxin genes that causes food poisoning in humans. Furthermore, the inclusion of Bt spores makes formulation for administration to humans and animals both more difficult, as spores are difficult to work with, and less efficient, since gram-for-gram any formulation would necessarily include a significant amount of inactive ingredient (spore) along with active ingredient (crystal). Separation of spores from crystal proteins is difficult as the two are very similar in size.

Accordingly, there remains an urgent need in the art for new approaches to delivering protein therapeutics such as anthelmintic proteins to the GI tract.

SUMMARY

The instant disclosure is based on the discovery that a sporulation defective or sporulation incompetent bacterium can be employed for production of highly purified preparations of nematicidal crystals suitable for pharmaceutical use. The purified nematicidal crystal preparations of the invention offer superior anti-helminthic properties to crystal proteins purified from spore crystal lysate (SCL). Moreover, such preparations are substantially free of contaminating spores and host bacterial proteins which are unsuitable for administration to humans. In certain exemplary embodiments, the preparations are substantially free of soluble cell components, lipids, and cell wall debris.

In one aspect, the instant disclosure provides a pharmaceutical composition comprising an isolated native, bioactive nematicidal crystal formed from a single type of nematicidal crystal protein. The nematicidal crystal protein is produced by a non-sporulating form of host bacterium, and the pharmaceutical composition is substantially free of any bacterial spores or host bacterial proteins other than nematicidal crystal protein in the form of a crystal.

In certain embodiments, the pharmaceutical composition includes excipients suitable for oral administration to a human subject. In certain embodiments, the host bacterium is a *Bacillus* species. In some embodiments, the host bacterium is a *Bacillus thuringiensis* (Bt). In some embodiments, the host bacterium is an *Escherichia coli* or *Pseudomonas fluorescens* species.

In some embodiments, the non-sporulating host bacterium is genetically engineered to have a genetic mutation that results in a defect in sporulation such that the native, bioactive nematicidal crystal is trapped in the cytosol of the bacterium. In certain embodiments, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In one embodiment, the genetic mutation resulting in a defect of sporulation is the deletion or inactivation of the spo0A gene.

In some embodiments, the host bacterium is genetically engineered to express the single type of nematicidal crystal protein under the control of a non-sporulation specific promoter. In certain embodiments, the non-sporulation specific promoter is a Cry3A, GerA, GNAT, or TadA promoter. In certain embodiments, the single type of nematicidal crystal protein is selected from the group consisting of Cry5B, Cry5C, Cry5D, Cry6A, Cry13A, Cry14A, Cry21A, Cry21B, Cry 55B, and variants and truncations thereof. In certain embodiments, the nematicidal crystal protein is Cry5B, or variants or fragments thereof. In some embodiments, the nematicidal crystal protein is Cry5B variant Ser407Cys.

In certain embodiments of the pharmaceutical compositions disclosed herein, the pharmaceutical compositions further comprise a second crystal protein in the form of an isolated native, bioactive nematicidal crystal formed from only the second crystal protein.

In some embodiments, the pharmaceutical composition comprises at least 95% isolated native, bioactive nematicidal crystal content.

In some embodiments the isolated native, bioactive nematicidal crystals are in an orally-available dosage form. In some embodiments, the pharmaceutical composition is in a dry powdered form and is encapsulated by a pharmaceutical capsule.

In another aspect, the disclosure provides a method for producing a pharmaceutical composition of the invention, the method comprising: (a) growing a non-sporulating form of a host bacterium that is genetically engineered to express a single type of nematicidal crystal protein, wherein the non-sporulating host bacterium produces native, bioactive nematicidal crystals formed from the single type of nematicidal crystal protein, wherein the host bacterium is grow in a growth medium, and optionally wherein the non-sporulating host bacterium releases the native, bioactive nematicidal crystals into the growth medium; and (b) isolating and concentrating the native, bioactive nematicidal crystals to form isolated, native, bioactive nematicidal crystals.

In some embodiments of this method, the host bacterium is a *Bacillus* species. In some embodiments, the host bacterium is a *Bacillus thuringiensis* (Bt). In some embodiments, the host bacterium is an *E. coli* or *P. fluorescens* species.

In some embodiments of the methods, the non-sporulating host bacterium is genetically engineered to have a genetic mutation that results in a defect in sporulation such that the native, bioactive nematicidal crystal is trapped in the cytosol of the bacterium. In some embodiments, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In some embodiments, the genetic mutation resulting in a defect of sporulation is the deletion or inactivation of the spo0A gene.

In certain embodiments of the method above, the host bacterium is genetically engineered to express the single type of nematicidal crystal protein under the control of a non-sporulation specific promoter. In certain embodiments, the non-sporulation specific promoter is a Cry3A, GerA, GNAT, or TadA promoter. In certain embodiments, the single type of nematicidal crystal protein is selected from the group consisting of Cry5B, Cry5C, Cry5D, Cry6A, Cry13A, Cry14A, Cry21A, Cry21B, Cry55B, and variants and truncations thereof. In certain embodiments, the nematicidal crystal protein is Cry5B, or variants or fragments thereof. In some embodiments, the nematicidal crystal protein is Cry5B variant Ser407Cys.

In certain embodiments, the method further comprises a step of exposing the non-sporulating host bacterium to an antimicrobial compound to inactivate the host bacterium. In certain embodiments, the antimicrobial compound is iodine. In certain embodiments, the antimicrobial compound is a pharmaceutical antibiotic. In certain embodiments, the antimicrobial compound is a beta-lactam antibiotic. In certain embodiments, the antimicrobial compound is an organic solvent selected form the group consisting of a terpene, hexane, and formaldehyde. In certain embodiments, the antimicrobial compound is a terpene. In certain embodiments, the terpene is selected from the group consisting of thymol, eugenol, geraniol, carvacrol, and citral, or a combination thereof. In certain embodiments, the terpene is carvacrol. In certain embodiments, the antimicrobial compound is hexane.

In certain embodiments, the method includes a step of adding a food-grade oil to the inactivated host bacterium to extract the inactivating agent from the nematicidal crystal protein. In certain embodiments, the food-grade oil is selected from the group consisting of corn oil, soybean oil, coconut oil, cottonseed oil, olive oil, palm oil, peanut oil, rapeseed oil, safflower oil, and sunflower oil. In some embodiments, the food-grade oil is corn oil. In some embodiments, the food-grade oil is corn oil. In certain embodiments, the method includes a step of a step of adding an organic solvent to the inactivated host bacterium to extract cell components from the nematicidal crystal protein. In certain embodiments, the organic solvent is hexane. In certain embodiments, the hexane is added to the inactivated host bacterium to 50% v/v. In certain embodiments, the method includes a step of centrifuging the mixture of organic solvent and inactivated host bacterium to pellet the nematicidal crystal protein.

In certain embodiments, the method further includes a step of homogenizing the inactivated host bacterium to form a bacterial lysate that includes the native, bioactive nematicidal crystals. In some embodiments, the method further includes a step of concentrating the bacterial lysate. In certain embodiments, the step of concentrating the bacterial lysate is selected from the group consisting of centrifugation, ultrafiltration, and diafiltration.

In some embodiments, the method further comprises a step of formulating the isolated native, bioactive nematicidal crystals in an orally-available dosage form. In some embodiments, the step of formulating comprises lyophilizing or spray-drying the isolated native, bioactive nematicidal crystals. In some embodiments, the step of formulating comprises encapsulating the isolated native, bioactive nematicidal crystals in a pharmaceutical-grade capsule.

In still another aspect, the disclosure provides a method for producing a pharmaceutical composition, including: (a) growing a non-sporulating form of a host bacterium that is engineered to express a single type of nematicidal crystal protein, wherein the non-sporulating host bacterium produces native bioactive nematicidal crystals formed from the single type of nematicidal crystal protein; (b) inactivating the grown non-sporulating host bacterium by exposing the grown non-sporulating host bacterium to an antimicrobial compound; (c) homogenizing the inactivated non-sporulating host bacterium to form a bacterial lysate; and (d) concentrating the native bioactive nematicidal crystals in the bacterial lysate to form isolated native, bioactive nematicidal crystals.

In some embodiments, this method further comprises a step of concentrating the grown nonsporulating host bacterium before inactivating the grown non-sporulating host bacterium. In some embodiments, the host bacterium is a *Bacillus* species. In some embodiments, the host bacterium is a *Bacillus thuringiensis* (Bt). In certain embodiments, the host bacterium is an *E. coli* or *P. fluorescens* species.

In some embodiments of this method, the non-sporulating host bacterium is genetically engineered to have a genetic mutation that results in a defect in sporulation such that the native, bioactive nematicidal crystal is trapped in the cytosol of the bacterium. In some embodiments, the genetic mutation resulting in a defect of sporulation is the deletion or inactivation of one or more genes selected from the group consisting of: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. In certain embodiments, the genetic mutation resulting in a defect of sporulation is the deletion or inactivation of the spo0A gene.

In some embodiments of the method, the host bacterium is genetically engineered to express the single type of nematicidal crystal protein under the control of a non-sporulation specific promoter. In certain embodiments, the non-sporulation specific promoter is a Cry3A, GerA, GNAT, or TadA promoter. In certain embodiments, the single type of nematicidal crystal protein is selected from the group consisting of Cry5B, Cry5C, Cry5D, Cry6A, Cry13A, Cry14A, Cry21A, Cry21B, Cry55B, and variants and truncations thereof. In certain embodiments, the nematicidal crystal protein is Cry5B, or variants or fragments thereof. In some embodiments, the nematicidal crystal protein is Cry5B variant Ser407Cys.

In some embodiments of the methods, the antimicrobial compound is iodine. In other embodiments of the methods, the antimicrobial compound is a pharmaceutical antibiotic. In some embodiments of the methods, the antimicrobial compound is a beta-lactam antibiotic. In some embodiments, the antimicrobial compound is an organic solvent selected from the group consisting of a terpene, hexane, or formaldehyde. In certain embodiments, the antimicrobial compound is a terpene. In some embodiments, the terpene is selected from the group consisting of thymol, eugenol, geraniol, carvacrol, and citral, or a combination thereof. In certain embodiments, the terpene is carvacrol. In certain embodiments, the antimicrobial compound is hexane.

In some embodiments, the method further comprises a step of extracting the antimicrobial compound from the inactivated host bacterium. In certain embodiments, the method includes a step of adding a food-grade oil to the inactivated host bacterium to extract the inactivating agent from the nematicidal crystal protein. In certain embodiments, the food-grade oil is selected from the group consisting of corn oil, soybean oil, coconut oil, cottonseed oil, olive oil, palm oil, peanut oil, rapeseed oil, safflower oil, and sunflower oil. In some embodiments, the food-grade oil is corn oil. In certain embodiments, a step of adding an organic solvent to the inactivated host bacterium to extract cell components from the nematicidal crystal protein. In certain embodiments, the organic solvent is hexane. In certain embodiments, the hexane is added to the inactivated host bacterium to 50% v/v. In certain embodiments, the method includes a step of centrifuging the mixture of organic solvent and inactivated host bacterium to pellet the nematicidal crystal protein.

In some embodiments, the method includes a step of formulating the isolated native, bioactive nematicidal crystals in an orally-available dosage form. In some embodiments, the method includes the step of formulating comprises lyophilizing or spray drying the isolated native, bioactive nematicidal crystals. In some embodiments, the step of formulating comprises encapsulating the isolated purified native, bioactive nematicidal crystals in a pharmaceutical-grade capsule.

In yet another aspect, the disclosure provides a method of treating a parasitic worm infection in a subject comprising: administering to the subject a therapeutically effective amount of a pharmaceutical composition comprising isolated native, bioactive nematicidal crystals formed from a single type of nematicidal crystal protein, wherein the pharmaceutical composition does not contain bacterial spores.

In some embodiments of the method of treating, the nematicidal crystal protein is selected from the group consisting of Cry5B, Cry5C, Cry5D, Cry6A, Cry13A, Cry14A, Cry21A, Cry21B, Cry55B, and variants and truncations thereof. In some embodiments, the nematicidal crystal protein is Cry5B. In some embodiments, the nematicidal crystal protein is Cry5B variant Ser407Cys.

In some embodiments of the method of treating, the composition further comprises a second crystal protein in the form of an isolated native, bioactive nematicidal crystal formed from only the second crystal protein. In some embodiments, the pharmaceutical composition comprises at least about 95% isolated native, bioactive nematicidal crystal. In some embodiments, the composition is in a dry powdered form and is encapsulated by a pharmaceutical capsule.

BRIEF DESCRIPTION OF THE DRAWINGS

FIG. 1A is depicts the positions of conserved blocks among certain Cry proteins. de Maagd, R. A., et al. "How *Bacillus thuringiensis* has evolved specific toxins to colonize the insect world." Trends in Genetics 17(4): 193-99, 195 (FIG. 2a) (April 2001). FIG. 1B illustrates the positions of conserved blocks among certain Cry proteins. Schnepf, E., et al. "*Bacillus thuringiensis* and Its Pesticidal Crystal Proteins." Microbiology and Molecular Biology Reviews 62(3): 775-806, 781 (FIG. 3) (September 1998).

FIG. 2 illustrates the amino acid sequence of Cry5Ba1 [SEQ ID NO:1].

FIG. 3 illustrates the amino acid sequence of Cry13Aa1 [SEQ ID NO:2].

FIG. 4 illustrates the amino acid sequence of Cry14Aa1 [SEQ ID NO:3].

FIGS. 5A-5C show amino acid sequences of other crystal proteins. FIG. 5A illustrates the amino acid sequence of Cry21Aa1 [SEQ ID NO:4]. FIG. 5B illustrates the amino acid sequence of Cry21Aa2 (98% identical to Cry21Aa1) [SEQ ID NO:5]. FIG. 5C illustrates the amino acid sequence of Cry6A [SEQ ID NO:6].

DETAILED DESCRIPTION

Figure 1A:
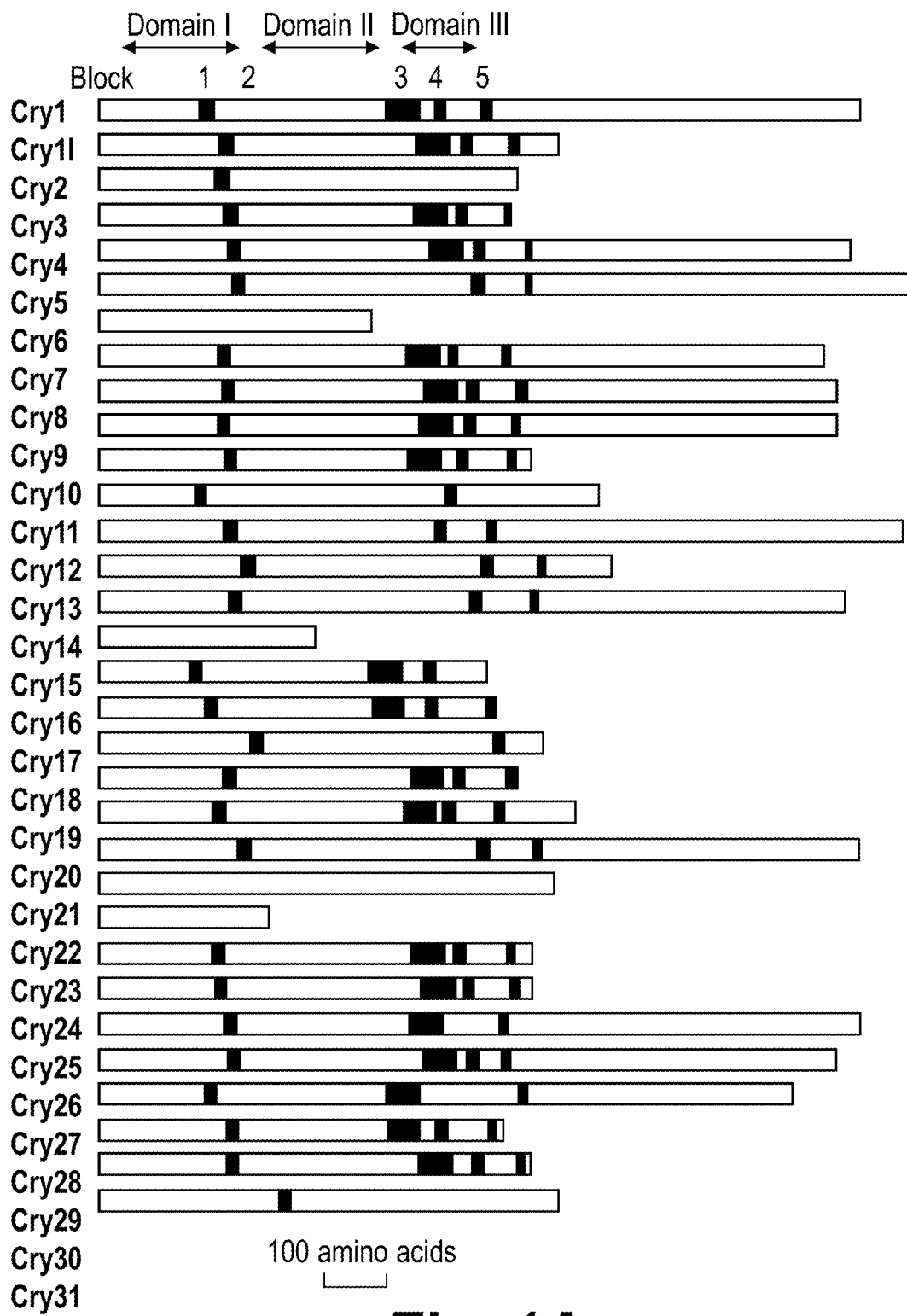
FIGS. 1A-1B are diagrams showing conserved blocks of amino acids in wild-type crystal proteins.

Disclosed are compositions of purified nematicidal crystal proteins, methods for making such purified nematicidal crystal proteins, and methods for treating or preventing STH infection by administering to a subject a preparation of purified nematicidal crystal proteins.

Microbes

In certain embodiments, the bacteria of the disclosure are non-sporulating bacteria. As used herein, the term "non-sporulating bacterium" includes wild-type bacteria that are incapable of producing spores (e.g., certain Gram-negative bacteria) as well as genetic variants of spore-forming bacteria that have been engineered to be defective in sporulation (e.g., certain Gram-positive bacteria). As used herein, unless the context makes clear otherwise, "a mutation resulting in a defect in sporulation" or "a genetic mutation that results in a defect in sporulation" refers to any genetic mutation that results in a defect in a member of the sporulation pathway and/or any genetic mutation that prevents the formation of viable spores. For example, non-sporulating bacteria and their creation are described in International Patent Application No. PCT/US2017/013436, incorporated herein by reference.

In some embodiments, sporulation-deficient bacteria are advantageous. An example of a sporulation-deficient bacterium is a spo0A-*Bacillus thuringiensis*. Any mutation or combination of mutations that confers sporulation deficiency but that does not substantially affect viability or heterologous gene expression can be used. These mutations include but are not limited to mutations in the following genes: kinA, kinB, spo0A, spo0B, spo0E, spo0F, spo0J, spo0M spoIIB, spoIID, spoIIE, spoIIF, spoIIG, spoIIL, spoIIM, spoIIIA, spoIIIB, spoIIIE, spoIVA, spoIVC, spoIVD, spoVG, spoVK, spoVL, spoVM, spoVN, spoVP, spoVQ, spoVID, σH, σF, σE, σG, and σK. (Silvaggi, J., et al. *Unmasking novel sporulation genes in Bacillus subtillus*. J Bacteriol. 186, 8089-8095, 2004; Sandman, K., et al. *Genetic Analysis of Bacillus subtilis spo Mutations Generated by Tn917-Mediated Insertional Mutagenesis*. Genetics. 117, 603-617, 1987; Malvar and Baum, Tn5401 *Disruption of the spoOF Gene, Identified by Direct Chromosomal Sequencing, Results in CryIIIA Overproduction in Bacillus thuringiensis*. J Bacteriol. 176, 4750-4753, 1994).

In some embodiments, an engineered sporulation deficiency may also render the host bacterium deficient in production in other crystal proteins and other virulence-associated products of sporulation. For example, spo0A-Bt does not produce Cry5B or other endotoxins such as Cry1, Cry4, or Cry8. In some embodiments, the genes of other Cry proteins and/or accessory proteins may be deleted or inactivated to ensure that no additional Cry proteins are used to form the protein crystal.

In such embodiments of sporulation-deficient bacteria, the sporulation-deficient bacteria may be engineered to express a single crystal protein gene such as Cry5B that is under control of a promoter that is actively and/or highly expressed prior to the sporulation phase of a bacterium, e.g., during the vegetative growth or stationary phase. Such engineered bacteria allow for only a single crystal protein to be expressed, and the resulting nematicidal crystals are homogenously comprised of only a single type of crystal protein. In certain embodiments, the promoter is heterologous (i.e., a non-sporulation specific promoter). In one embodiment, the promoter is a Cry3A, GerA, GNAT, or TadA promoter.

In some embodiments, strains of non-sporulating bacteria that autolyse at the end of their growth cycle may be used. Such autolysing bacteria may be used, such that a homogenization step during the purification process may be avoided or reduced.

Bacteria are particularly applicable to the control of STHs because 1) recombinant bacteria can cheaply express large amounts of Cry proteins prior to administration into the GI tract of a mammalian subject, and Cry proteins so expressed, independent of any Cry proteins that may be secreted by bacteria in the GI tract, have been shown to have a significant impact on STHs, 2) studies using purified Cry protein to treat hookworms, whipworms, and *H. bakeri*, all in infected rodents, demonstrate that STHs in the mammalian GI tract can ingest and be killed/intoxicated by Cry proteins, 3) recombinant bacteria expressing a therapeutic protein, in which the protein is not purified, are cheaper to produce since no protein purification steps are needed, and 4) recombinant bacteria delivering STH curing proteins (e.g., Cry5B) are more effective that purified proteins (e.g., Cry5B) at the same bio-active protein dose (e.g., total Cry5B) in curing infections.

Microbes of the disclosed compositions and methods include killed and inactivated forms of *Bacillus* sp., including *Bacillus subtilis* (e.g., *B. subtilis* natto, and *B. subtilis* PY79), *B. cereus*, (e.g., *B. cereus* var. *Toyoi* (*Toyocerin*), *B. cereus* var. *toyoii*), *B. toyonensis*, *B. clausii*, *B. pumilus* and *B. thuringiensis*. *B. subtilis* has been extensively characterized as a safely ingested food additive in humans. In certain exemplary embodiments, killed and inactive forms of *B. thuringiensis* are used.

Other useful bacteria include but are not limited to non-sporulating variants of *Lactococcus* sp., *Bifidobacterium* sp., *Streptococcus* sp., *Clostridium* sp., *Sporolactobacillus* sp, *Sporosarcina* sp., *Brevibacillus* sp, *Leuconostoc* sp., *Pediococcus* sp., *Enterococcus* sp. and *Escherichia* sp. *Lactobacillus* sp. includes but is not limited to *L. lactis*, *L. casei*, *L. paracasei*, *L. acidophilus*, *L. bulgaricus*, *L. delbrueckii* subsp. *bulgaricus*, *L. helveticus*, *L. plantarum*, *L. salivarius*, *L. reuteri*, *L. gasseri*, and *L. animalis*. *Bifidobacterium* sp. includes but is not limited to *B. animalis*, *B. bifidum*, *B. breve*, *B. infantis*, and *B. longum*. *Streptococcus* sp. includes but is not limited to *S. thermophilus*. *Clostridium* sp. includes but is not limited to *Clostridium butyricum*. *Sporolactobacillus* sp. includes but is not limited to *Sporolactobacillus vineae*. *Sporosarcina* sp. includes but is not limited to *Sporosarcina pasteurii*. *Brevibacillus* sp. includes but is not limited to *Brevibacillus laterosporus*.

Still other useful bacteria useful in connection with present disclosure include forms of Gram-negative bacteria. In certain exemplary embodiments, the Gram-negative bacteria include *E. coli* species (e.g., NISSLE 1917) and *Pseudomonas* species (e.g., *Pseudomonas fluorescens*). Exemplary Cry-expressing Gram-negative bacteria which can be killed or inactivated by the methods of the present disclosure include the Cry-expressing *E. coli* strain of Ge et al. ("Hyperexpression of a *Bacillus thuringiensis* delta-endotoxin-encoding gene in *Escherichia coli*: properties of the product", *Gene*, 93: 49-54 (1990)) and the *P. fluorescens* strain of Peng et al. ("A Delta-endotoxin encoded in *Pseudomonas fluorescens* displays a high degree of insecticidal activity", *App. Microbiol Biotech.*, (2003), 63:300-306).

Nematicidal Proteins

As used herein, unless the context makes clear otherwise, "nematicidal protein" refers to any protein that has toxic activity against nematodes or helminthes. Exemplary nematicidal proteins include crystal proteins such as the anthelmintic Cry proteins (e.g., Crickmore et al., 1998 *Microbiology and Molecular Biology Reviews* 62(3): 807-813; Schnepf et al., 1998 *Microbiology and Molecular Biology Reviews* 62(3): 775-806; including but not limited to the *B. thuringiensis* Cry proteins Cry5B (e.g., SEQ ID NO:1) and its subvariants, Cry13A (e.g., SEQ ID NO:2) and its subvariants, Cry14A (e.g., SEQ ID NO:3) and its subvariants, Cry21A (e.g., SEQ ID NOS:4-5) and its subvariants, and Cry6A and its subvariants (e.g., SEQ ID NO:6)) in the bacterium for delivery into a helminth (e.g., roundworm)-infected vertebrate animal gastrointestinal tract via oral dosing (gavage, drinking, eating, pill, capsule, powder, etc.). The Cry proteins are expressed in the cytosol of the bacterium and form crystals, allowing access to the anthelmintic protein after the bacterium lyses or opens up. Nematicidal crystals formed from nematicidal crystal proteins (such as Cry proteins) induce toxicity in worms and helminths by solubilizing or decrystalizing to release the individual nematicidal crystal proteins, thereby allowing the crystal protein to act directly on worms and helminths.

The nematicidal crystals described herein are more stable than the individual crystal proteins of which they are formed, and are resistant to proteolysis. Crystal proteins expressed by bacterium as described herein form crystals of between about 100 kDa and about 170 kDa, between about 110 kDa and about 160 kDa, between about 120 kDa and about 150 kDa, between about 125 kDa and about 145 kDa, or between about 130 kDa and about 140 kDa. These crystal proteins come together to form much larger nematicidal crystals.

Each nematicidal crystal may have a size of about 100 nm, about 200 nm, about 300 nm, about 400 nm, about 500 nm, about 600 nm, about 700 nm, about 800 nm, about 900 nm, about 1000 nm, about 1100 nm, about 1200 nm, about 1300 nm, about 1400 nm, about 1500 nm, about 1600 nm, about 1700 nm, about 1800 nm, about 1900 nm, or about 2000 nm along its longest axis.

In some embodiments, the nematicidal crystals described herein may be between about 100 nm and about 2000 nm, between about 200 and about 2000 nm, between about 300 nm and about 2000 nm, between about 400 nm and about 2000 nm, between about 500 nm and about 2000 nm, between about 600 nm and about 2000 nm, between about 700 nm and about 2000 nm, between about 800 nm and about 2000 nm, between about 900 nm and about 2000 nm, between about 1000 nm and about 2000 nm along its longest axis.

In some embodiments, the nematicidal crystals described herein may be between about 100 nm and about 1000 nm, between about 200 and about 1000 nm, between about 300 nm and about 1000 nm, between about 400 nm and about 1000 nm, between about 500 nm and about 1000 nm, between about 600 nm and about 1000 nm, between about 700 nm and about 1000 nm, between about 800 nm and about 1000 nm, between about 900 nm and about 1000 nm, between about 1000 nm and about 1000 nm along its longest axis.

In certain embodiments, purified nematicidal crystals formed from a first type of nematicidal crystal protein (e.g. Cry5B) may be combined with nematicidal crystals formed from a second type of nematicidal crystal protein (e.g. Cry5C, Cry5D, Cry6A, Cry13A, Cry14A, Cry21A, Cry21B, or Cry55B) in a single pharmaceutical formulation. In such embodiments, a single formulation allows the GI tract to be seeded with multiple forms of purified nematicidal crystals simultaneously. For example, due to the lack of cross-resistance between Cry5B-resistant roundworms and Cry21A-resistant roundworms, simultaneous administration of Cry5B and Cry21A in the gastrointestinal tract may inhibit the development of parasite resistance to the combination therapy.

In the long run, removing antibiotic selection capability (e.g., genetic selection markers) from the plasmids that are used to introduce heterologous Cry protein-encoding sequences, as well as using bacterial strains that are unable to replicate outside the vertebrate host, may be desirable in order to environmentally contain the genetically modified bacteria. For example, LAB (Lactic Acid Bacteria) have been engineered to be autotrophic in thymidine or thymine synthesis such that they can only grow in the vertebrate intestine where thymidine or thymine is present and not in the environment where thymidine or thymine is not present. See, e.g., Steidler L, et al. "Biological containment of genetically modified *Lactococcus lactis* for intestinal delivery of human interleukin 10." Nat Biotechnol 21: 785-789 (2003).

Cry-transformed bacteria such as Bacilli or LAB may be cultured and expression of intracellular, membrane-anchored, or secreted Cry protein by such bacteria may be confirmed using antibodies raised against each Cry protein and standard Western blotting or ELISA techniques.

To assess the bioactivity of all constructs, recombinant bacteria expressing Cry protein (full length, truncated, or variants) may be fed to the free-living nematode, *C. elegans*. Cry protein toxicity on *C. elegans* using LC50, brood-size, developmental inhibition assays on solid media and in liquid wells may then be quantitated. *C. elegans* can access the Cry proteins either via protein secreted onto the solid media/into the liquid well or by their ability to grind, open and digest bacteria. Confirmation that the recombinant bacteria are making bioactive Cry proteins may be obtained. Furthermore, the bioactivity (e.g., $LC_{50}$ in μg/mL) may be quantified and the constructs giving the highest activity determined.

Truncations, Variants, and Sub-Variants

The crystal proteins may be truncated to enhance their effectiveness. The usefulness of Bt toxins (e.g., crystal proteins) for controlling STHs may be limited by the protein size that STHs can ingest. Some parasitic roundworms poorly ingest proteins larger than about 40 kDa. Thus, the effectiveness of any particular Bt toxin may be limited by size exclusion of proteins that STHs take in and so should be small enough to be readily absorbed by the STH gut while retaining toxic activity. A truncated toxin may be easier to express in bacteria. Producing a truncated toxin also alleviates the requirement that the target STH has the proper proteases present to correctly process full length protoxin (which is inactive) to a truncated, active toxin form. Thus, a truncated toxin is immediately available for intoxication independent of whether the proper protease processing enzymes are present in the STH target. Truncated toxin may also express at a higher level in microbes because truncated toxins are soluble and less likely to form insoluble inclusions in the cell expressing them, which could be toxic to the cell or which could make the toxin fold incorrectly. Accordingly, it is desirable to produce truncated Bt toxin fragments (e.g., crystal protein fragments). Moreover, fragments of certain Bt toxins have been tested and shown to retain toxic activity and have improved biological properties. By "truncated," when referring to a Bt toxin protein (crystal protein) is meant a Bt toxin protein that is not full-length but retains at least 5%, 10%, 20%, 30%, 40%, 50%, 60%, 70%, 80%, or 90% or more of the toxic activity of a corresponding full-length Bt toxin protein.

"Variants" or "subvariants" of Cry proteins include polypeptides with one or more substitutions, e.g., no more than 20 substitutions, alternatively no more than 10 substitutions, or substitutions at 10% or fewer of the residues, relative to a corresponding wild-type polypeptide or truncated version thereof. The variant, subvariant, or truncated polypeptide has at least 5%, 10%, 20%, 30%, 40%, 50%, 60%, 70%, 80%, or 90% of the activity, e.g., toxic activity, of the corresponding wild-type polypeptide or truncated version. Conservative substitutions include substitutions within the following groups: glycine, alanine, threonine, valine, isoleucine, leucine; aspartic acid, glutamic acid, asparagine, glutamine; serine, cysteine; lysine, arginine; aspartic acid, glutamic acid; serine, threonine; asparagine, glutamine; phenylalanine, tyrosine. One exemplary variant Cry protein is Cry5B with cysteine substituted for serine at position 407 (Ser407Cys) (SEQ ID NO: 7).

Figure 1B:
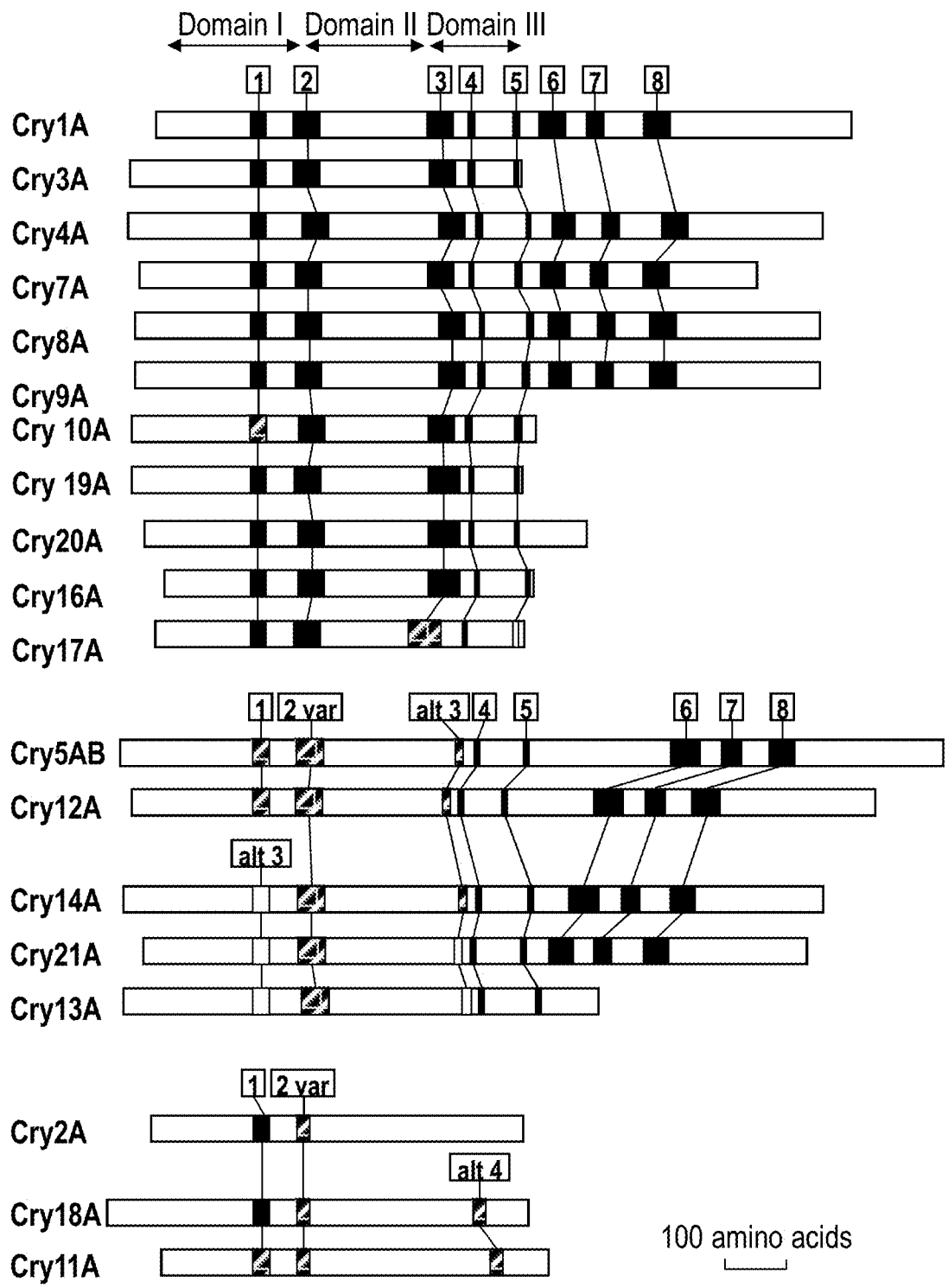

The crystal proteins may be full length, truncated, variants, or subvariants. The truncated crystal protein may include any truncation of the N- and C-termini that still retains toxin activity. The truncated form is not full-length but retains at least 5%, 10%, 20%, 30%, 40%, 50%, 60%, 70%, 80%, or 90% or more of the toxic activity of a corresponding full-length Bt toxin protein. For example, the truncated portion may be truncated between the end of conserved block 5 and the C-terminus of the full-length protein. FIGS. 1A and 1B schematically compare the numbered conserved amino acid blocks (1-5) for a variety of Cry proteins.

In one embodiment, the truncated crystal protein may contain the toxin domain of the crystal protein and optionally include up to 5, 10, or 20 additional amino acids. The truncated crystal protein may be truncated after a conserved amino acid sequence of block 5 and optionally include up to 5, 10, or 20 additional amino acids. The conserved amino acid sequence of block 5 may contain the motif DRIEF (SEQ ID NO: 23), DRLEF (SEQ ID NO: 24), or some other related sequence as well as surrounding amino acid residues, e.g., three amino acids upstream and two amino acids downstream of this motif. Table 1 shows the block 5 sequences for various Cry proteins. See e.g., Schnepf, E., et al., *Bacillus thuringiensis* and Its Pesticidal Crystal Proteins, *Microbiology and Molecular Biology Reviews* 62(3): 775-806, (e.g., at p. 781, FIG. 3) (September 1998); and Crickmore et al., Revision of the Nomenclature for the *Bacillus thuringiensis* Pesticidal Crystal Proteins, *Microbiology and Molecular Biology Reviews* 62(3): 807-813 (September 1998). The truncated crystal protein may also be truncated at the N-terminus. For example, the truncated crystal protein may not contain the first about 1, 2, 3, 4, 5, 6, 7, 8, 9, 10, 15, 20, 25, 30, 35, 40, 45, or 50 amino acids at the N-terminus.

Cry protein variants can exhibit at least 50, 55, 60, 65, 70, 75, 80, 85, 86, 87, 88, 89, 90, 91, 92, 93, 94, 95, 96, 97, 98, or 99 percent amino acid sequence identity to a known Cry protein sequence such as any that are disclosed in Crickmore et al., 1998 *Microbiology and Molecular Biology Reviews* 62(3): 807-813, or in Schnepf et al., 1998 *Microbiology and Molecular Biology Reviews* 62(3): 775-806, including full length Cry proteins and truncated Cry proteins, Cry protein variants or subvariants thereof. Also contemplated according to certain embodiments are polynucleotides encoding such Cry proteins and truncations and variants thereof.

TABLE 1

| Protein | Block 5 Conserved Group |
|---|---|
| Cry1A | VYIDRIEFVP (SEQ ID NO: 7) |
| Cry3A | VYIDKIEFIP (SEQ ID NO: 8) |
| Cry4A | VLIDKIEFLP (SEQ ID NO: 9) |
| Cry5A | VFLDRIEFIP (SEQ ID NO: 10) |
| Cry5B | LFLDRIEFVP (SEQ ID NO: 11) |
| Cry7A | FYVDSIEFIP (SEQ ID NO: 12) |
| Cry8A | VYIDRIEFIP (SEQ ID NO: 13) |
| Cry9A | VYVDRIEFIP (SEQ ID NO: 14) |
| Cry10A | IYIDKIEFIP (SEQ ID NO: 15) |
| Cry12A | MVLDRIEFVP (SEQ ID NO: 16) |
| Cry13A | IYLDRLEFVP (SEQ ID NO: 17) |
| Cry14A | IFIDRIEFIP (SEQ ID NO: 18) |
| Cry19A | LILDKIEFLP (SEQ ID NO: 19) |
| Cry20A | FVLDKIELIP (SEQ ID NO: 20) |
| Cry21A | LFLDRIEFIS (SEQ ID NO: 21) |
| Consensus | i-iDkIEFiP (SEQ ID NO: 22) |

In Table 1, the consensus sequence denotes the positions at which at least 75% of the aligned proteins in the group have an identical or conserved amino acid sequence. An uppercase letter in the sequence indicates that at least 75% of the residues at that position are identical. A lowercase letter indicates that at least 75% of the residues at that position are conserved. Conserved amino acids fall into the following groups: a (A, G, S, T, or P); d (D, E, N, or Q); f (F, W, or Y), I (I, L, M, or V), and k (K or R).

The truncated crystal protein may be a truncated form of Cry5B such as *B. thuringiensis* Cry5B (FIG. 2). Truncated Cry5B may extend from about amino acid 1, 2, 3, 4, 5, 6, 7, 8, 9, 10, 15, 20, 25, 30, 35, 40, 45, or 50 to at least about amino acid 693. The truncated form of Cry5B may optionally include up to an additional 5, 10, 20, 30, 40, or 50 amino acids from the C-terminus after conserved block 5, e.g., through about 698, 703, 713, 723, 733, or 743.

The truncated crystal protein may be a truncated form of Cry13A such as *B. thuringiensis* Cry13A (FIG. 3). Truncated Cry13A may extend from about amino acid 1, 2, 3, 4, 5, 6, 7, 8, 9, 10, 15, 20, 25, 30, 35, 40, 45, or 50 to at least about amino acid 688. The truncated form of Cry13A may optionally include up to an additional 5, 10, 20, 30, 40, or 50 amino acids from the C-terminus after conserved block 5, e.g., through about 693, 698, 708, 718, 728, or 738.

The truncated crystal protein may be a truncated form of *B. thuringiensis* Cry14A (FIG. 4). Truncated Cry14A may extend from about amino acid 1, 2, 3, 4, 5, 6, 7, 8, 9, 10, 15, 20, 25, 30, 35, 40, 45, or 50 to at least about amino acid 675. The truncated form of Cry14A may optionally include up to an additional 5, 10, 20, 30, 40, or 50 amino acids from the C-terminus after conserved block 5, e.g., through about 680, 685, 695, 705, 715, or 725.

The truncated crystal protein may be a truncated form of Cry21A such as *B. thuringiensis* Cry21Aa1 (FIG. 5A) or Cry21Aa2 (FIG. 5B). Truncated Cry21A may extend from about amino acid 1, 2, 3, 4, 5, 6, 7, 8, 9, 10, 15, 20, 25, 30, 35, 40, 45, or 50 to at least about amino acid 685. The truncated form of Cry21A may optionally include up to an additional 5, 10, 20, 30, 40, or 50 amino acids from the C-terminus after conserved block 5, e.g., through about 690, 695, 705, 715, 725, or 735.

Nucleic acid molecules encoding amino acid sequence variants, truncated versions, or both, of a Cry protein are prepared by a variety of methods known in the art. These methods include, but are not limited to, isolation from a natural source (in the case of naturally occurring amino acid sequence variants) or preparation by, for example, oligonucleotide-mediated (or site-directed) mutagenesis, PCR mutagenesis, and cassette mutagenesis of an earlier prepared variant or a non-variant version of protein. Moreover, the present technology includes synthetic nucleic acid molecules where nucleotides are modified to include codons preferred in a particular organism, remove codons rarely used in a particular organism, or remove sequences that may inhibit transcription or RNA processing and the like.

Cry protein truncations may at least include conserved blocks 1-5. As seen in FIGS. 1A and 1B, alignment of known Cry toxins reveals five conserved sequence blocks (blocks 1-5) that are common to a majority of the proteins and are thought to be located in the active toxin domain. See de Maagd, R. A., et al. "How *Bacillus thuringiensis* has evolved specific toxins to colonize the insect world." Trends in Genetics 17(4): 193-99 (April 2001). Comparison of the carboxy-terminal halves of the sequences have suggested the presence of three additional blocks that lie outside of the active toxic core. See Schnepf, E., et al. "*Bacillus thuringiensis* and Its Pesticidal Crystal Proteins." Microbiology and Molecular Biology Reviews 62(3): 775-806 (September 1998). Thus, Cry protein truncations may be truncated after the conserved amino acid sequence of block 5 (e.g., DRIEF (SEQ ID NO: 23) or DRLEF (SEQ ID NO: 24)). Alternatively, Cry protein truncations may be truncated after the conserved amino acid sequence of block 5 (e.g., DRIEF (SEQ ID NO: 23) or DRLEF (SEQ ID NO: 24)) plus an additional about 2, 3, 4, 5, 10, 15, 20, 25, 30, 35, 40, 45, or 50 amino acids of the c-terminal domain.

The complete amino acid sequence of Cry5Ba1 is listed in FIG. 2. The conserved amino acid sequence DRIEF (SEQ ID NO: 23) in Cry5B ends at amino acid number 693. Thus, a truncated form of Cry5B may include at least amino acids 50 through about 693. A truncated form of Cry5B may extend from about amino acid 1, 2, 3, 4, 5, 6, 7, 8, 9, 10, 15, 20, 25, 30, 35, 40, 45, or 50 to at least about amino acid 693. Alternatively, or in addition to, a truncated form of Cry5B may include about 5, 10, 15, 20, 25, 30, 35, or 40 additional amino acids of the c-terminal domain.

The complete amino acid sequence of Cry13Aa1 is listed in FIG. 3. The conserved amino acid sequence DRLEF (SEQ ID NO: 24) in Cry13A ends at amino acid number 688. Thus, a truncated form of Cry13A may include at least amino acids 50 through about 688. A truncated form of Cry5B may extend from about amino acid 1, 2, 3, 4, 5, 6, 7, 8, 9, 10, 15, 20, 25, 30, 35, 40, 45, or 50 to at least about amino acid 688. Alternatively, or in addition to, a truncated form of Cry13A may include about 5, 10, 15, 20, 25, 30, 35, or 40 additional amino acids of the c-terminal domain.

The complete amino acid sequence of Cry14Aa1 is listed in FIG. 4. The conserved amino acid sequence DRIEF (SEQ ID NO: 23) in Cry14A ends at amino acid number 675. Thus, a truncated form of Cry14A may include at least amino acids 50 through about 675. A truncated form of Cry5B may extend from about amino acid 1, 2, 3, 4, 5, 6, 7, 8, 9, 10, 15, 20, 25, 30, 35, 40, 45, or 50 to at least about amino acid 675. Alternatively, or in addition to, a truncated form of Cry14A may include about 5, 10, 15, 20, 25, 30, 35, or 40 additional amino acids of the c-terminal domain.

The complete amino acid sequence of Cry21Aa1 and Cry21Aa2 are listed in FIG. 5A and FIG. 5B, respectively. The amino acid sequence of Cry21Aa2 is about 98% identical to the sequence of Cry21Aa1. The conserved amino acid sequence DRIEF (SEQ ID NO: 23) in Cry21A ends at amino acid number 685. Thus, a truncated form of Cry21A may include at least amino acids 50 through about 685. A truncated form of Cry5B may extend from about amino acid 1, 2, 3, 4, 5, 6, 7, 8, 9, 10, 15, 20, 25, 30, 35, 40, 45, or 50 to at least about amino acid 685. Alternatively, or in addition to, a truncated form of Cry21A may include about 5, 10, 15, 20, 25, 30, 35, or 40 additional amino acids of the c-terminal domain.

Anthelmintic Experiments

Once heterologous Cry protein expression and bioactivity are confirmed in a desired bacterium, the modified bacteria may be used for curative-type and preventative-type anthelmintic experiments.

Antibody production: Antibodies against recombinant Cry proteins (e.g., Cry5B, Cry21A, Cry14A, Cry13A, and Cry6A, full length and truncated proteins) may be produced and purified according to standard methodologies (e.g., *Current Protocols in Immunology*, John Wiley & Sons, New York, N.Y. (2009).

Bioactivity tests: To assess the bioactivity of all constructs, recombinant bacilli or other bacteria expressing heterologous Cry proteins are fed to the free-living nematode, *C. elegans. C. elegans* can access the Cry proteins either via protein secreted onto the solid media/into the liquid well, by protein naturally released as bacteria break open, or by their ability to grind and digest bacteria to open the bacterial cells.

Rodent and parasite tests: Three intestinal parasitic nematodes—*H. bakeri* (small intestine nematode parasite) in mice, and *Trichuris muris* (whipworm) in mice, and *A. ceylanicum* (hookworm) in hamsters are tested. The tests address: 1) where in the GI tract do heterologous Cry-expressing bacteria reside and for how long; and 2) how do these bacteria affect the acquisition and progression of intestinal nematode parasites.

Parasite tests: Naïve (uninfected) mice are gavaged with the best heterologous Cry-protein expressing recombinant bacterial strain(s) based on expression and bioactivity. Protect against progression test: Mice are infected with *H. bakeri*. Two weeks later, infected mice are treated with heterologous Cry-protein expressing or control bacteria, respectively. Intestinal worm burdens and fecal egg counts are used to determine if the recombinant bacteria provide anthelmintic therapy in mice with pre-existing nematode infections.

Exemplary Parasites

The disclosed methods relate to the control of parasitic worms, e.g., nematodes and platyhelminths, using crystal proteins from *Bacillus* and their derivatives. Parasitic worms within the scope of the invention include but are not limited to those in Class Adenophorea, e.g., Order Mononchida, Family Plectidae, and Order Stichosomida, Family Mermithidae and Tetradonematidae; Class Secernentea, e.g., Order Rhabditida, Family Carabonematidae, Cephalobidae, Chambersiellidae, Heterorhabditidae, Oxyuridae, Panagrolaimidae, Rhabditidae, Steinernematidae, Syrphonematidae, Syrphonematidae, or Thelastomatidae; Order Spirurida, Family Filariidae, Onchocercidae, Physalopteridae, Syngamidae, Spiruridae, Subuluridae, or Thelaziidae; Order Diplogasterida, Family Diplogasteridae; and Order Tylenchida, Family Allantonematidae, Aphelenchidae, Aphelenchoididae, Entaphelenchidae, Fergusobiidae, Phaenopsitylenchidae, Sphaerulariidae, Anguinidae, Dolichodoridae, Belonolaimidae, Pratylenchidae, Hoplolamidae, Heteroderidae, Criconematidae, Tylenchulidae or Tylenehidae. In one embodiment, the parasite is from Class Secernentea, Order Ascaridida, Family Ascarididae; Class Adenophorea, Order Trichurida, Family Trichuridae; Class Secernentea, Order Strongylida, Family Ancylostomatidae (ancylostomidae) or Trichostrongylidae; or Class Secernentea, Order Spirurida, Family Dracunculidae, Filariidae, or Onchocercidae.

The parasite may be a helminth. Helminths within the scope of the invention include but are not limited to those from Phylum Annelida, Class Polychaetae, Class Myzostomida, Class Clitellata, Subclass Hirudinea, Order Gnathobdellidae, Order Rhynchobdellidae; Phylum Platyhelminthes (Flatworms), Class Turbellaria, Class Monogenea, Order Monopisthocotylea, Order Polyopisthocotylea, Class Trematoda, Subclass Aspidogasrea, Subclass Digenea; Super Order Anepitheliocystida, Order Strigeatida, Family Schistosomatidae, Subfamily Schistosomatinae, Genus *Schistosoma*, Order Echinostomatida, Family Fasciolidae, Family Paramphistomatidae, Family Echinostomatidae; Super Order Epitheliocystida, Order Plagiorchiida, Family Dicrocoeliidae, Family Troglotrematidae, Order Opisthorchiida, Family Heterophyidae, Family Opisthorchiidae, Class Cestoda, Subclass Cestodaria, Subclass Eucestoda, Order Pseudophyllidea, Family Diphyllobothriidae, Order Cyclophyllidea, Family Taeniidae, Family Hymenolepididae, Family Dilepididae, Family Mesocestoididae, Order Tetraphyllidea, Order Proteocephalata, or Order Spatheobothridea. For example, Cry proteins with the scope of the invention may be employed to prevent, inhibit or treat Roundworm, Whipworm, Hookworm, Schistosome, or Trematodes.

The parasite may also be gastrointestinal tract parasitic roundworms/nematodes. The gastrointestinal tract parasitic roundworms/nematodes may include but are not limited to the following species: *Haemonochus, Cooperia, Ostertagia, Trichostrongylus, Teladorsagia, Nematodirus, Ancylostoma, Cyathostominea/Cyathostomin/Cyathostome, Strongylus, Parascaris, Ascaris, Trichuris, Oesophagostomum/Oesophagustomum, Trichiuris, Bunostomum, Oxyuris, Chabertia, Habronema, Draschia, Triodontophorus, Toxocara, Toxascaris,* and *Uncinaria. Haemonochus* species includes but is not limited to *Haemonchus contortus* and *Haemonchus placei, Cooperia* species includes but is not limited to *Cooperia oncophora, Cooperia pectinata,* and *Cooperia curticei. Ostertagia* species includes but is not limited to *Ostertagia ostertagi, Ostertagia (Teladorsagia) circumcincta,* and *Ostertagia trifurcate. Trichostrongylus* species includes but is not limited to *Trichostrongylus axei, Trichostrongylus colubriformis,* and *T. circumcincta. Teladorsagia* species includes but is not limited to *Teladorsagia (Ostertagia) circumcincta. Nematodirus* species includes but is not limited to *Nematodirus spathiger. Ancylostoma* species includes but is not limited to *Ancylostoma caninum, Ancylostoma braziliense,* and *Ancylostoma tubaeforme.*

Cyathostominea/Cyathostomin/Cyathostome nematodes are also included. *Strongylus* species (small and large) includes but is not limited to *Strongylus vulgaris, Strongylus equinus,* and *Strongylus edentatus. Parascaris* species includes but is not limited to *Parascaris equorum. Strongyloides* species includes but is not limited to *Strongyloides westeri. Ascaris* species includes but is not limited to *Ascaris suum. Trichuris* species includes but is not limited to *Trichuris globulosa, Trichuris suis, Trichuris campanula,* and *Trichuris vulpis. Oesophagostomum/Oesophagustomum* species includes but is not limited to *Oesophagustomum dentatum, Oesophagustomum quadrispinulatum, Oesophagostomum columbianum,* and *Oesophagustomum venulosum. Trichiuris* species includes but is not limited to *Trichiuris ovis. Bunostomum* species includes but is not limited to *Bunostomum trigonocephalum. Oxyuris* species includes but is not limited to *Oxyuris equi* (pin worms). *Chabertia* species includes but is not limited to *Chabertia ovina. Habronema* species includes but is not limited to *Habronema microstoma* and *Habronema muscae. Draschia* species includes but is not limited to *Draschia megastoma. Triodontophorus* species includes but is not limited to *Triodontophorus minor* and *Triodontophorus serrates. Toxocara* species includes but is not limited to *Toxocara canis* and *Toxocara cati.* Toxascaris species includes but is not limited to Toxascaris leonine. *Uncinaria* species includes but is not limited to *Uncinaria stenocephala.* Human parasitic roundworms of the gastrointestinal tract include but are not limited to the hookworms *Ancylostoma duodenale* and *Necator americanus,* the whipworm *Trichuris trichiura,* the roundworm *Ascaris lumbricoides,* the threadworm *Strongyloides stercoralis,* and the pinworm *Enterobius vermiculari.*

Additional Therapeutic Agents

In certain embodiments, the pharmaceutical compositions of the invention are administered in combination with at least one additional therapeutic agent. This additional agent can be, for example, a small molecule or a polypeptide (including antibodies and fragments thereof). In a further embodiment, the additional therapeutic is a nicotinic acetylcholine receptor agonist. In certain embodiments, the additional therapeutic agent is administered simultaneously with the pharmaceutical compositions of the invention. In certain embodiments, the additional therapeutic agent is administered sequentially (and in either order) with the pharmaceutical composition. In certain embodiments, the nicotinic acetylcholine receptor agonist is from the levamisole family of nicotinic acetylcholine receptor agonists. In certain embodiments, the nicotinic acetylcholine receptor agonist is levamisole. In certain embodiments, the levamisole is administered in an amount of about 0.1 mg/kg to about 5.0 mg/kg. In certain embodiments, the nicotinic acetylcholine receptor agonist is pyrantel or tribendimidine. In certain embodiments, the pyrantel is administered in an amount of about 1.0 mg/kg to about 15.0 mg/kg. In certain embodiments, the tribendimidine is administered in an amount of about 0.25 mg/kg to about 10 mg/kg.

Administration, Dosage Forms, Pharmaceutical Compositions

The present invention contemplates administration of purified crystal proteins to the gastrointestinal tract of a subject. The pharmaceutical compositions may thus be formulated for oral administration. Oral administration is preferably in an aqueous suspension, emulsion, powder or solid. The composition may be formulated into a food or added to food by the user prior to consumption. Administration to the gastrointestinal tract may also be in the form of an anal suppository (e.g., in a gel or semi-solid formulation). All such formulations are made using standard methodologies.

The methods of treatment disclosed herein are typically practiced on any animal where inhibiting pathogen or parasites is desired. In certain embodiments, the animal is a human. However, the animal can be any livestock or zoological specimen where such inhibition of parasites/pathogens provides economic and health benefits. Any animal can benefit by the claimed methods, including birds, reptiles, mammals such as horses, cows, sheep, goats, pigs, and the like domesticated animals, or any of a variety of animals of zoological interest. Other purposes are readily apparent to one skilled in the arts of nutrient absorption, feed utilization and bioavailability.

The present invention further contemplates a therapeutic system for treating, reducing and/or controlling parasitic infections. Typically, the system is in the form of a package containing a therapeutic composition of the present invention, or in combination with packaging material. The packaging material includes a label or instructions for use of the components of the package. The instructions indicate the contemplated use of the packaged component as described herein for the methods or compositions of the invention. By way of example, and not of limitation, a system can comprise one or more unit dosages of a therapeutic composition according to the present invention. Alternatively, the system can alternately contain bulk quantities of a therapeutic composition. The label contains instructions for using the therapeutic composition in either unit dose or in bulk forms as appropriate, and may also include information regarding storage of the composition, disease indications, dosages, routes and modes of administration and the like information.

Furthermore, depending upon the particular contemplated use, the system may optionally contain either combined or in separate packages one or more of the following components: bifidogenic oligosaccharides, flavorings, carriers, and the like components. One embodiment comprises unit dose packages of purified nematicidal crystal protein for use in combination with a conventional liquid product, together with instructions for combining the purified nematicidal crystal protein with the formula for use in a therapeutic method.

Different dosage regimens may be used in the disclosed methods. In some embodiments, a daily dosage is administered once, twice, three times, or four times a day for one, two, three, four, five, six, seven, eight, nine, or ten days. In some embodiments, a once- or twice-daily dosage is administered every other day.

Administration of the compositions containing the active ingredients effective in inhibiting parasite growth in the intestine and in feces generally consist of one to ten unit dosages of 10 mg to 10 g per dosage of the composition for one day up to one month for a human of approximately 100 kg body weight. Unit dosages are generally given once every twelve hours and up to once every four hours. Preferably two to four dosages of the composition per day, each comprising about 0.1 g to 50 g per dosage, for one to seven days are sufficient to achieve the desired result.

In various specific embodiments, an effective dose of a composition of the present disclosure can be in a range of from about 0.01 mg/kg to about 100 mg/kg for an adult patient, more preferably between about 0.1 mg/kg and about 10 mg/kg of the disclosed composition. Effective doses can be administered to a subject at any suitable frequency, e.g., at least once a week, preferably once a day. Pediatric dosages may be in the range of 15% to 90% of adult dosages.

In other embodiments, a constant dosage of the composition can be administered over time, for example about 2 gm to about 4 gm per day, up to about 6 g to about 10 g per day, depending on the severity of the physiological condition. Once the infection has been effectively ameliorated, the subject can in many instances decrease the dosage to about 2 gm to about 4 gm per day for maintenance purposes. The desired dose may be presented in multiple (e.g., two, three, four, five, six, or more) sub-doses administered at appropriate intervals throughout the day.

The pharmaceutical compositions of the invention can be administered via any of the accepted modes of administration or agents known in the art. However, oral administration is preferred because this route of delivery delivers the purified nematicidal crystal protein to the GI tract. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, and can be in unit dosage forms suitable for simple administration of precise dosages. One exemplary embodiment of the dose form is a capsule containing the composition of the disclosure including the purified nematicidal crystal protein in a dried form, blended with pharmaceutical carrier. The capsule for such a dose form can be of any suitable type, e.g., a gelatin capsule of a conventional variety.

The physiologically compatible carrier medium with which the purified nematicidal crystal proteins are employed, can be of any simple type, e.g., a pharmaceutically acceptable carrier such as fructo-oligo-saccharide (FOS) medium, or other soluble fiber, sugar, nutrient or base material for the composition, with which the bacterial species can be formulated, e.g., in an orally administrable form. Other carrier media include mannitol, inulin (a polysaccharide), polydextrose, arabinogalactan, polyols lactulose, lactitol, etc. A wide variety of materials can be used as carrier material in the practice of the present disclosure, as will be apparent to those of ordinary skill in the art, based on the description herein.

The carrier medium, when present, can be blended with the bacterial species in any suitable amounts, such as an amount of from 5% to 95% by weight of carrier medium, based on the total weight of the bacterial species and the carrier medium, in various embodiments. In other embodiments, the amount of carrier medium may be in a range having a lower limit of any of 5%, 10%, 12%, 15%, 20%, 25%, 28%, 30%, 40%, 50%, 60%, 70% or 75%, and an upper limit, higher than the lower limit, of any of 20%, 22%, 25%, 28%, 30%, 40%, 50%, 60%, 70%, 75%, 80%, 85%, 90%, and 95%. The amount of carrier medium in a specific embodiment may be determined based on considerations of the specific dose form, relative amounts of the purified nematicidal crystal protein, the total weight of the composition including the carrier medium and the bacterial species, and the physical and chemical properties of the carrier medium, and other factors, as known to those of ordinary skill in the probiotic and pharmaceutical formulation art.

In certain embodiments, the purified nematicidal crystal proteins are formulated in a composition that protects the Cry proteins from the acid environment of the stomach. Accordingly, the invention includes a composition containing a purified nematicidal crystal protein and a pharmaceutically-acceptable acid-resistant ("enteric") carrier. By acid-resistant is meant that the carrier or coating does not dissolve in an acidic environment. An acidic environment is characterized by a pH of less than 7. The acid-resistant carrier is resistant to acids at pH less than about 4.0. Preferably, the carrier does not dissolve in pH 2-3. Most preferably, it does not dissolve in pH of less than 2. To purified nematicidal crystal proteins from stomach acids, the purified nematicidal crystal protein are coated or encapsulated with the acid-resistant carrier.

In certain embodiments, the coating is pH-sensitive. For example, the coating may dissolve after the pH is greater than 4.0. For example, the coating dissolves in a neutral environment as is encountered in the small intestine, and does not dissolve in an acidic environment as is encountered in the stomach. Alternatively, the enteric coating dissolves when exposed to specific metabolic event such as an encounter with a digestive enzyme that is found in the small intestine. For example, the coating is digested by a pancreatic enzyme such as trypsin, chymotrypsin, or a pancreatic lipase. The formulation is hydrated in the small intestine. Digestion or dissolution of the coating allows liberation of purified nematicidal crystal proteins, e.g., purified Cry5B, into the intestine.

In other embodiments, purified nematicidal crystal proteins are stabilized in a gel or paste such as an anhydrous carbohydrate paste. In alternate formulations, the purified nematicidal crystal proteins are lyophilized and/or suspended in a gel or paste. Enteric coating materials are known in the art, e.g., malic acid-propane 1,2-diol. Cellulose derivatives, e.g., cellulose acetate phthalate or hydroxypropyl methylcellulose phthalate (HPMCP), are also useful in enteric acid-resistant coatings. Other suitable enteric coatings include cellulose acetate phthalate, polyvinyl acetate phthalate, hydroxypropylmethylcellulose phthalate and anionic polymers of methacrylic acid and methyl methacrylate. Another suitable enteric coating is a water emulsion of ethylacrylate methylacrylic acid copolymer, or hydroxypropyl methyl cellulose acetate succinate (HPMAS). (See, e.g., U.S. Pat. No. 5,591,433). An enteric coating is designed to resist solution in the stomach and to dissolve in the neutral or alkaline intestinal fluid.

In certain embodiments, the purified nematicidal crystal proteins are preferably formed into dry powders. Suitable drying methods include a natural drying, a forced-air drying, a spray drying, a freeze drying, and the like. Of those, a spray drying, drum drying or a forced-air drying are preferably used. A protective agent such as skim milk, sodium glutamate, and saccharides may be used in a time of drying. Saccharides, glucose, and trehalose may be used. In an example of freeze-drying, purified crystal protein may be frozen at −80° C. and then put into a FreeZone 1 Liter Benchtop Freeze Dry System (Labconco catalog number 7740020). The condenser is set to −60° C. and the vacuum is set at 22 mTor. The samples are freeze-dried overnight. In an example of spray-drying, a PCC sample at 10% solids w/v is spray dried using a Yamato Pulvis GB22 (or any other spray drying system) through a 100 micron atomizer nozzle at 5 mLs/min with atomizing air set at 1 Kgf/m$^2$, drying air set at 0.21 m$^3$/min, inlet/outlet temperatures set at 98° C./59° C., respectively.

Auxiliary and adjuvant agents may include, for example, preserving, wetting, suspending, sweetening, flavoring, perfuming, emulsifying, and dispensing agents. Prevention of the action of contaminating microorganisms, if desired, can be accomplished using various antibacterial and antifungal agents, such as, parabens, chlorobutanol, phenol, sorbic acid, and the like. Isotonic agents, such as sugars, sodium chloride, and the like, may also be included.

Solid dosage forms can be prepared with coatings and shells, such as enteric coatings and others well-known in the art. They can contain pacifying agents and can be of such composition that they release the active compound or compounds in a certain part of the intestinal tract in a delayed manner. Examples of embedded compositions that can be used are polymeric substances and waxes. The active compounds also can be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., the active agent (such as the purified nematicidal crystal protein), and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethyl formamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Actual methods of preparing such dosage forms are known, or will be apparent, to those skilled in this art. Reference is made, for example, to Remington's Pharmaceutical Sciences, 18th ed. (Mack Publishing Company, Easton, Pa., 1990).

Methods

The methods are directed to treating a parasitic worm or helminth infection in a subject comprising administering to the subject a therapeutically effective amount of a composition comprising isolated native, bioactive nematicidal crystals formed from a single type of nematicidal crystal protein. The pharmaceutical composition is substantially free of any bacterial spores or host bacterial proteins other than nematicidal crystal protein in the form of a crystal.

The methods are also directed to reducing the severity of a parasitic worm or helminth infection comprising administering to the subject a therapeutically effective amount of a pharmaceutical composition comprising isolated native, bioactive nematicidal crystals formed from a single type of nematicidal crystal protein, wherein the pharmaceutical composition is substantially free of any bacterial spores or host bacterial proteins other than nematicidal crystal protein in the form of a crystal.

Selected Definitions

As used herein, unless the context makes clear otherwise, "treatment," and similar words such as "treated," "treating" etc., indicates an approach for obtaining beneficial or desired results, including and preferably clinically desirable results. Treatment can involve optionally either the amelioration of symptoms of the disease or condition, or the delaying of the progression of the disease or condition.

As used herein, unless the context makes clear otherwise, "subject" means a vertebrate, such as a mammal. The mammal can be a feline, a rodent, a canine, a bovine, an equine, a swine, a caprine, an ovine, or a primate. In some embodiments, the subject is a human.

As used herein, unless the context makes clear otherwise, "reducing the likelihood of occurrence," "prevention," and similar words such as "prevented," "preventing" etc., include approaches for preventing, inhibiting, or decreasing the likelihood of the onset or recurrence of a disease or condition, in a manner that exhibits statistical significance, for example, when compared to the results obtained when the indicated method steps are omitted. Similarly, also included are preventing, inhibiting, or decreasing the likelihood of the occurrence or recurrence of the symptoms of a disease or condition, or optionally delaying the onset or recurrence of a disease or condition, or delaying the occurrence or recurrence of the symptoms of a disease or condition. As used herein, "prevention" and similar words also include reducing the intensity, effect, symptoms and/or burden of a disease or condition prior to onset or recurrence of the disease or condition. Methods according to these and related embodiments may be practiced using an effective amount or a therapeutically effective amount of an agent that substantially eradicates, reduces the severity of, or reduces the likelihood of occurrence of a soil-transmitted helminth (STH) infection. As used herein, an "effective amount" or a "therapeutically effective amount" of a composition, agent or substance is that amount sufficient to obtain a desired biological effect, such as beneficial results, including clinical results.

As used herein, unless the context makes clear otherwise, "food grade oil" includes oils suitable for ingestion by humans or animals. Exemplary food grade oils include, but are not limited to, oils extracted from vegetables, such as corn oil, soybean oil, coconut oil, cottonseed oil, olive oil, palm oil, peanut oil, rapeseed or canola oil, safflower oil, sunflower oil. Food grade oil includes, but is not limited to, nut oils, e.g. almond oil, beech nut oil, brazil nut oil, cashew oil, hazelnut oil, macadamia nut oil, mongongo nut oil, pecan oil, pine nut oil, pistachio oil, walnut oil, and pumpkin seed oil. Food grade oils include oils from citrus, fruit, melons and gourd seeds, or any edible plant.

In certain preferred embodiments, the compositions described herein for treating or reducing the severity or likelihood of occurrence of an STH infection are formulated as pharmaceutical compositions, which will preferably be formulated for oral delivery. Pharmaceutical compositions are formulated so as to allow the agent(s) contained therein to be bioavailable upon administration of the composition to a human.

It will be appreciated that the practice of the several embodiments of the present invention will use, unless indicated specifically to the contrary, conventional methods in virology, immunology, microbiology, molecular biology and recombinant DNA techniques that are within the skill of the art, and many of which are described below for the purpose of illustration. Such techniques are explained fully in the literature. See, e.g., *Current Protocols in Molecular Biology or Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references that are cited and discussed throughout the present specification. Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques may be used for recombinant technology, molecular biological, microbiological, chemical syntheses, chemical analyses, pharmaceutical preparation, formulation, and delivery, and treatment of patients.

As used herein, the terms "pure" and "purity" in combination with a number (e.g. 95% pure) refer to compounds and substances of the instant disclosure being present in weight/weight amount relative to other compounds and substances. For example, a composition that is 95% pure nematicidal crystal means that 95% of the composition (weight/weight) is nematicidal crystal protein and 5% of the composition (w/w) comprises one or more other substances.

As used herein, the phrase "crystal content" in combination with a percentage (e.g. 95% crystal content) refers to nematicidal crystals of the instant disclosure being present in a composition in the percentage of the total weight of the compositions. In certain embodiments, the compositions of the invention have at least 80%, at least 90%, or at least 95% (e.g., 95%, 96%, 97%, 98%, 99% or 100% crystal content.

As used herein, the term "substantially free of" in reference to a composition or compound (e.g. a compound substantially free of spores) means that the composition or compound contains less than or equal to 5% w/w of another substance (e.g. the compound has less than or equal to 5%, 2%, 1%, 0.5%, 0.1%, 0.01%, 0.001% or 0.0001% w/w of spores).

As used in this specification and the appended claims, the singular forms "a," "an" and "the" include plural references unless the content clearly dictates otherwise. Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Each embodiment in this specification is to be applied mutatis mutandis to every other embodiment unless expressly stated otherwise.

As used herein, the term "about" in quantitative terms refers to plus or minus 5% of the value it modifies (rounded up to the nearest whole number if the value is not subdividable, such as a number of molecules, nucleotides, or amino acids). For example, "about 20%" would encompass 15-20% and "about 80%" would encompass 75-85%, inclusive. Moreover, where "about" is used herein in conjunction with a quantitative term it is understood that in addition to the value plus or minus 5%, the exact value of the quantitative term is also contemplated and described. For example, the term "about 23%" expressly contemplates, describes, and includes exactly 23%.

EXAMPLES

The following Examples are presented by way of illustration and not limitation.

Example 1: Creation of IBaCC

For production of Cry5B in sporulation-defective cells, *B. thuringiensis* (Bt) strain 4D8 which lacks any crystal protein expressing (Identification of *Bacillus thuringiensis* subsp. kurstaki strain HD1-Like bacteria from environmental and human samples after aerial spraying of Victoria, British Columbia, Canada, with Foray 48B. Appl Environ Microbiol. 2001 March; 67(3):1035-43) and in which the master spo0A regulator of sporulation (spo0A-) was deleted by homologous recombination. This composition is further referred to as Cry5B-BaCC (*Bacillus* with Cytosolic Crystal).

To inactivate Cry5B-BaCC, the transformed *B. thuringiensis* 4D8 strain was propagated aerobically in 200 mL volume in 2 liter baffled flasks with shaking at 30° C. in three-fold concentrated Luria-Bertani broth (LB) supplemented with 10 µg/mL erythromycin and 200 µg/mL kanamycin for 48 hours. The transformed *B. thuringiensis* cells were spun down at 4500 rpm for one hour at 4° C. and resuspended to ¼ of the original cell culture volume with prechilled sterile double-distilled water, and then were treated with 1 mg/mL carvacrol (a food-grade antimicrobial) for 15 min with shaking at 4° C. The carvacrol-treated cells were spun down and washed three times with prechilled sterile double-distilled water. Final pellets were concentrated 40 times and were stored at −80° C. until use. The dead BaCC containing biologically active Cry5B crystals are termed IBaCC (Inactivated *Bacillus* with Cytosolic Crystal). The 4D8 strain is also capable of autolysis, naturally lysing at the end of the growth cycle and releasing the crystal. Killing with carvacrol and homogenization can still be used to kill any residual cells and break open any residual intact IBaCC.

Example 2: Purification of Cry5B from IBaCC Using Homogenization

Figure 6:
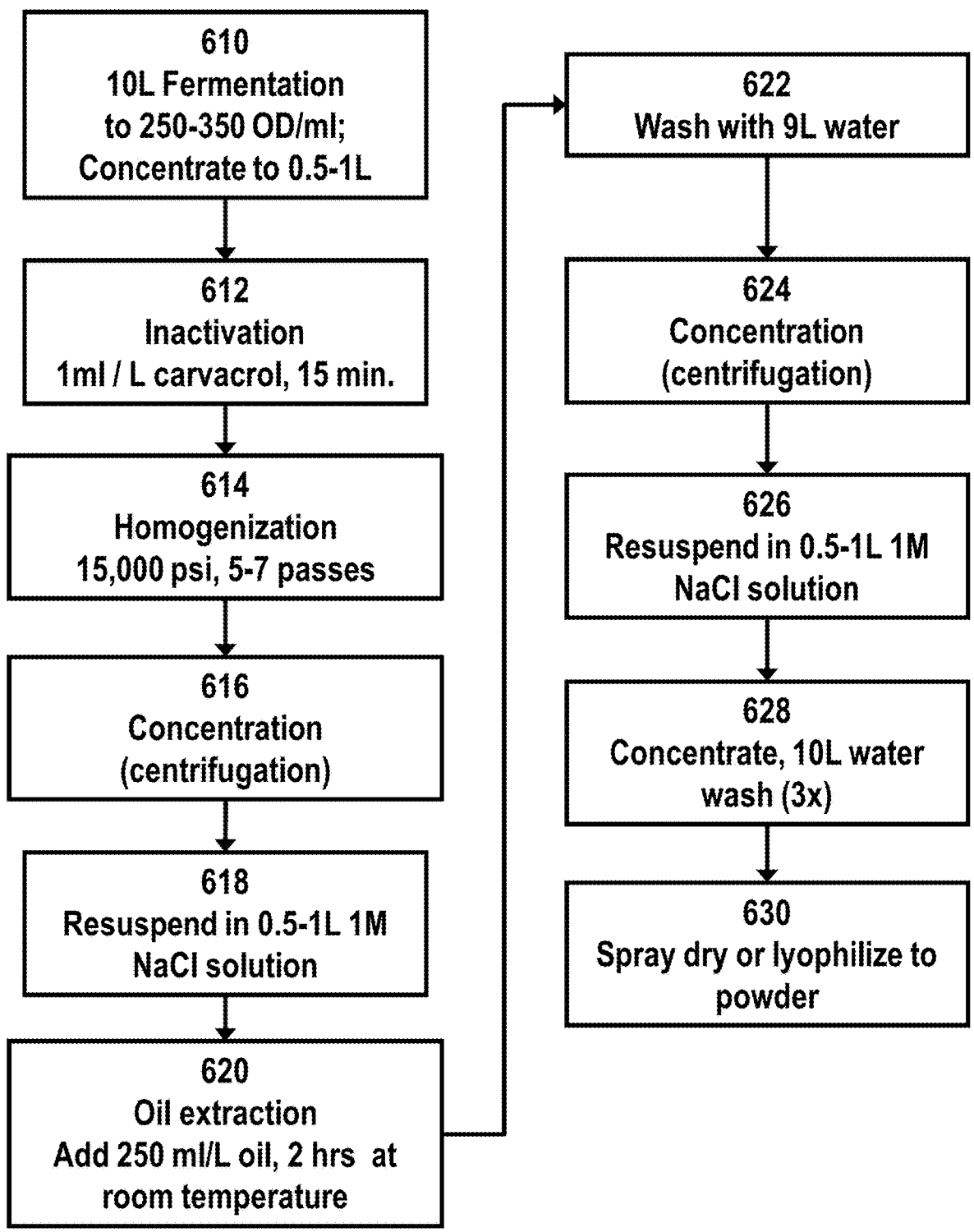
FIG. 6 is a flow chart showing the steps for purifying nematicidal crystal protein from inactivated BaCC (IBaCC).

FIG. 6 shows a flow chart of the process used to purify Cry5B crystal protein from IBaCC. To purify large amounts of Cry5B protein from IBaCC, a 10 L fermentation harvest was undertaken (FIG. 6, step 610). Ten liters of BaCC were grown to between 250-350 OD/ml. The BaCC was then concentrated to between 0.5 L and 1 L using centrifugation (8000×g, 30 minutes), and then inactivated by adding 1 ml/L carvacrol and stirring for 15 minutes at room temperature (step 612) to produce IBaCC. Other methods of concentrating the BaCC prior to the inactivation step may be used, such as ultrafiltration or diafiltration.

The IBaCC was homogenized at 15,000 psi for 5 to 7 passes (step 614), and the resulting lysate was centrifuged to concentrate the bacterial lysate (step 616). Other methods of concentrating the IBaCC may be used, such as ultrafiltration or diafiltration. The resulting pellet was resuspended in 0.5 L to 1 L of 1M NaCl solution (step 618). The concentrated lysate was then mixed with 250 ml/L oil for two hours at room temperature to extract the carvacol (step 620). Following the oil extraction, 9 L of water was then added (step 622), and the mixture was again concentrated (step 624) by centrifugation. The concentrated pellet was then resuspended in 0.5 L to 1 L of NaCl solution (step 626). The mixture was then washed three times with 10 L water and concentrated (step 628) by centrifugation (8000×g, 30 minutes). The resulting composition is a purified Cry5B crystal (PCC). In some embodiments, the composition may be spray-dried or lyophilized (step 630).

Figure 7:
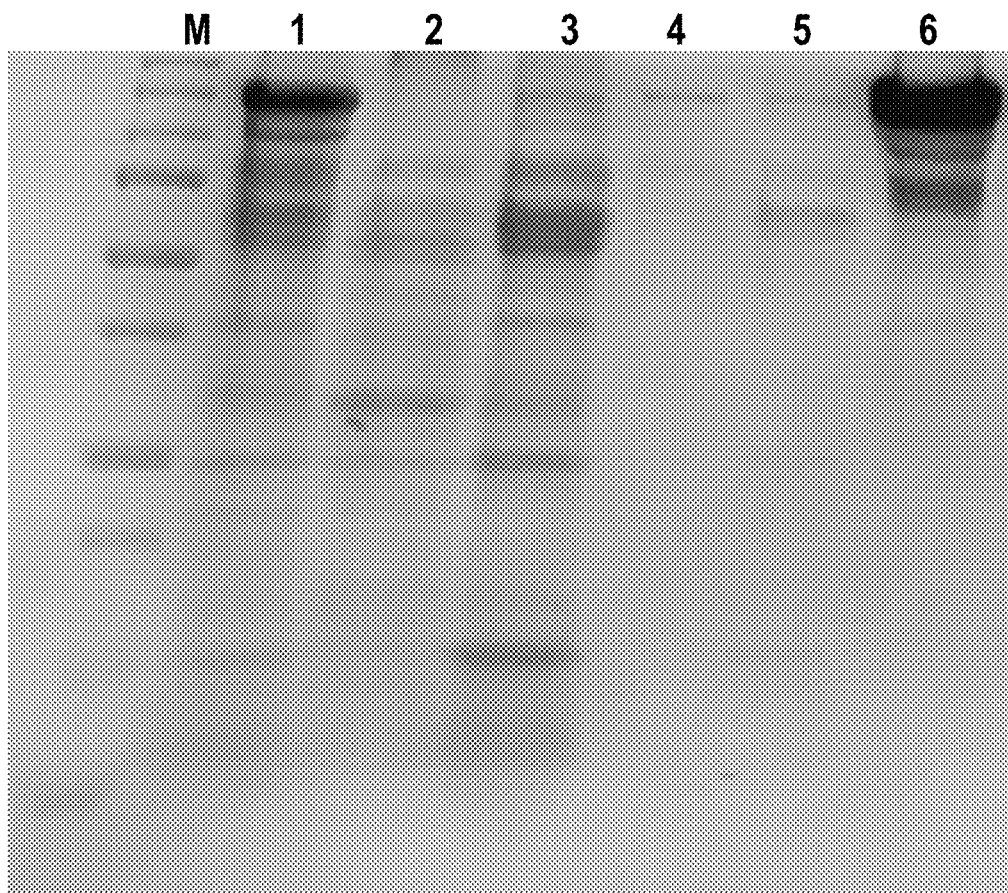
FIG. 7 is a picture of a protein gel with samples from several steps of the purifying process for Cry5B PCC.

FIG. 7 shows a protein gel with samples from various stages of the purification process. Lane 1 of the gel is 5 µL of homogenized IBaCC after being grown to 200 nm OD. Lane 2 is a 15 µL sample of supernatant from concentrated homogenized IBaCC. Lane 3 is a 15 µL sample of a water layer following washing of the oil-extracted IBaCC lysate. Lane 4 is a 15 µL sample of the 1M NaCl wash (step 626). Lane 5 is a 15 µL sample of a phosphate buffered saline wash of pelleted IBaCC. Lane 6 is a 15 µL sample of PCC following step 628 (from another batch of BaCC grown to an OD of 312 Absorbance 600 units).

Figure 8:
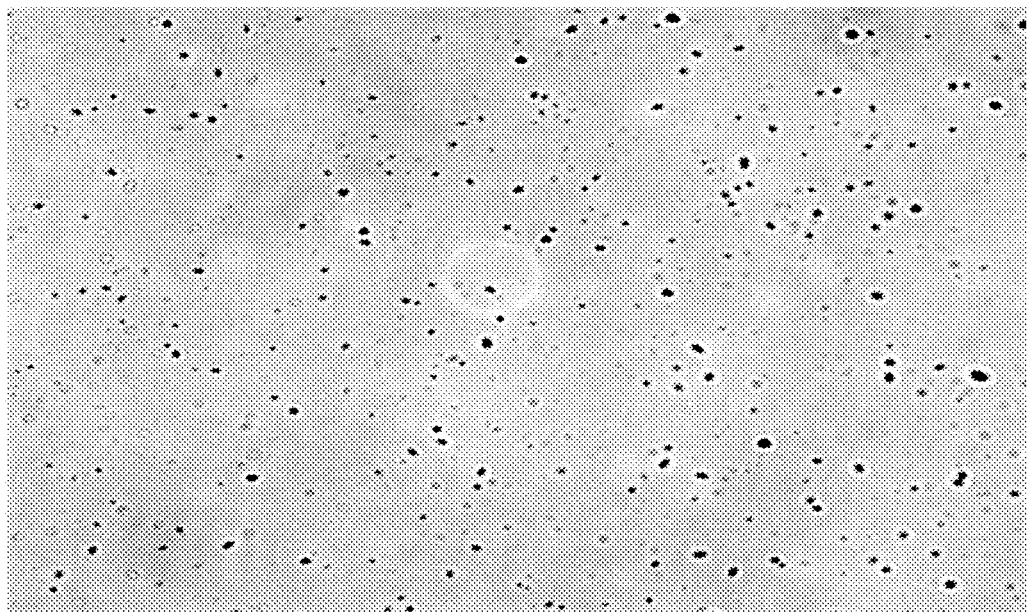
FIG. 8 is a phase-contrast photomicrograph of Cry5B PCC at 1000× magnification.

FIG. 8 is a phase-contrast photomicrograph of PCC particles at 1000× magnification.

Example 3: Purification of Cry5B from Autolyzed IBaCC

Some strains of BaCC, such as strain 4D8, autolyse at the end of their growth cycle. This autolysis can obviate or reduce the need for a homogenization step following inactivation with an antimicrobial compound. Thus, referring to purification flow chart of FIG. 6, the homogenization step 614 may be eliminated or the number of passes reduced if an autolysing strain of bacteria is used. In such embodiments, a 10 L fermentation harvest of an autolysing BaCC may be undertaken (FIG. 6, step 610). Ten liters of BaCC may be grown to between 250-350 OD/ml. The BaCC may then be concentrated to between 0.5 L and 1 L using centrifugation, and then inactivated by adding 1 ml/L carvacrol and stirring for 15 minutes at room temperature (step 612) to produce IBaCC. Since the IBaCC have autolysed before and/or after inactivation, homogenization was not necessary. Other methods of concentrating the BaCC prior to the inactivation step may be used, such as ultrafiltration or diafiltration.

The lysate from the autolysed IBaCC may then be concentrated by centrifugation, ultrafiltration, or diafiltration (step 616). The resulting pellet may then be resuspended in 0.5 L to 1 L of 1M NaCl solution (step 618). The concentrated lysate may then be mixed with 250 ml/L oil for two hours at room temperature to extract the carvacol (step 620). Following the oil extraction, 9 L of water may then be added (step 622), and the mixture may be concentrated again (step 624) by centrifugation, ultrafiltration, or diafiltration. The concentrated mixture may then be resuspended in 0.5 L to 1 L of NaCl solution (step 626). The mixture may then be washed three times with 10 L water and concentrated (step 628) by centrifugation, ultrafiltration, or diafiltration. The resulting composition will be a purified Cry5B crystal (PCC). In some embodiments, the composition may then be spray-dried or lyophilized (step 630).

Example 4: PCC Intoxicates Whipworms In Vitro

Figure 9A:
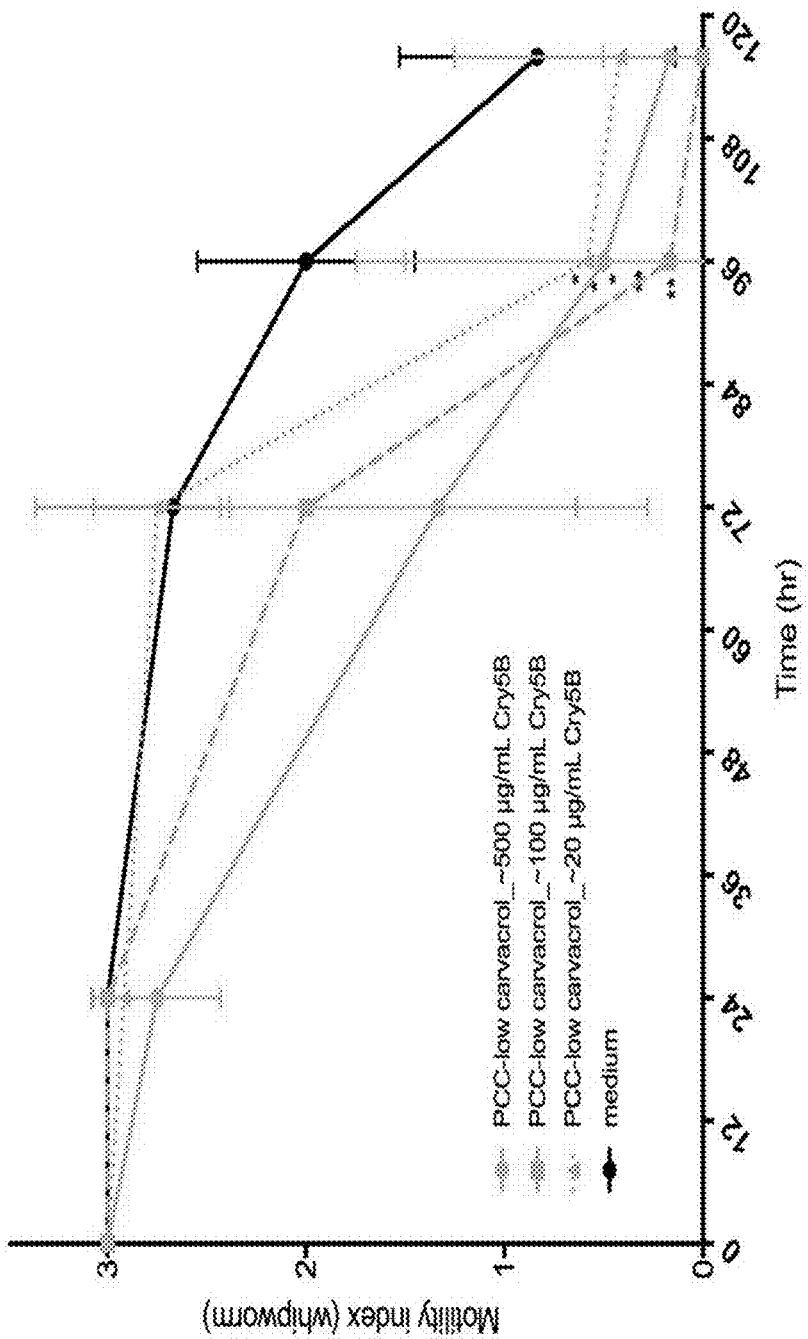
FIG. 9A shows a graph of changes in whipworm motility over time following in vitro exposure to doses of Cry5B PCC.
Figure 9B:
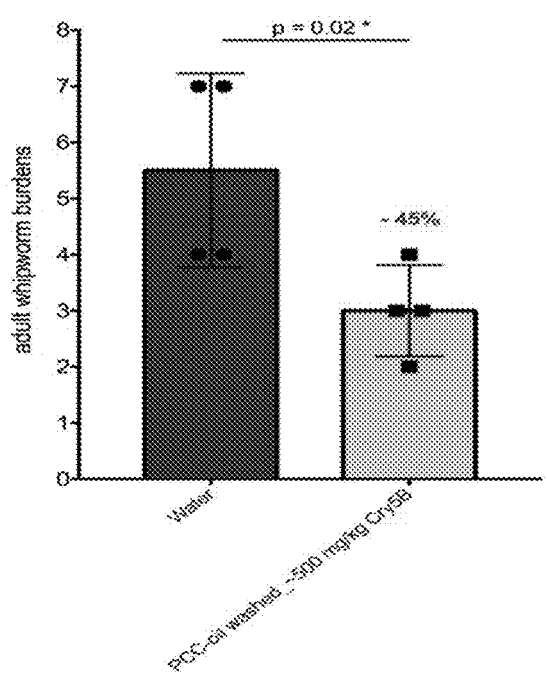
FIG. 9B shows a bar histogram of in vivo whipworm burdens in hamsters treated with Cry5B PCC and water control.
Figure 10A:
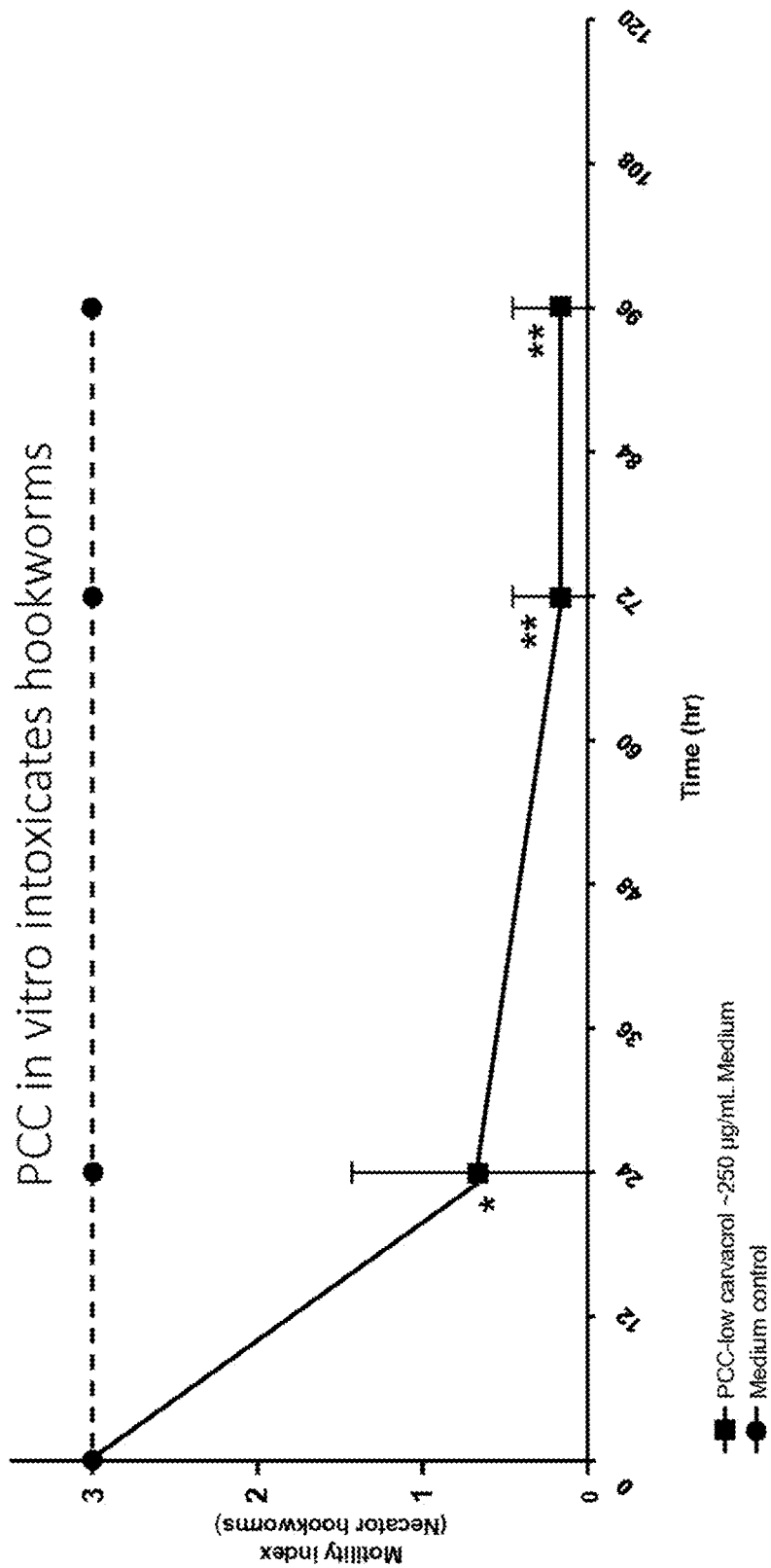
FIG. 10A shows a graph of changes in hookworm motility over time following in vitro exposure to doses of Cry5B PCC.
Figure 10B:
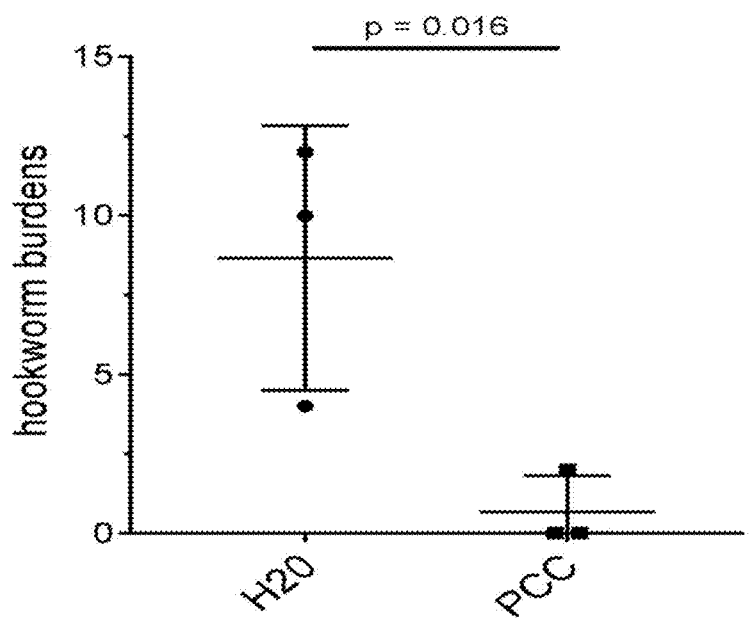
FIG. 10B shows a histogram of hookworm burdens in hamsters treated with Cry5B PCC and water control.
Figure 10C:
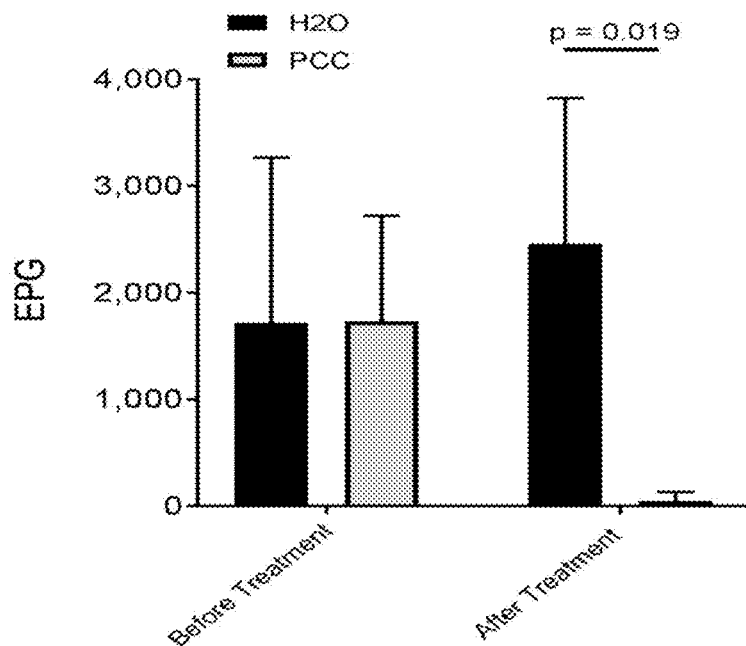
FIG. 10C shows a bar histogram of hookworm burdens in hamsters before and after treatment with Cry5B PCC and water control.
Figure 11A:
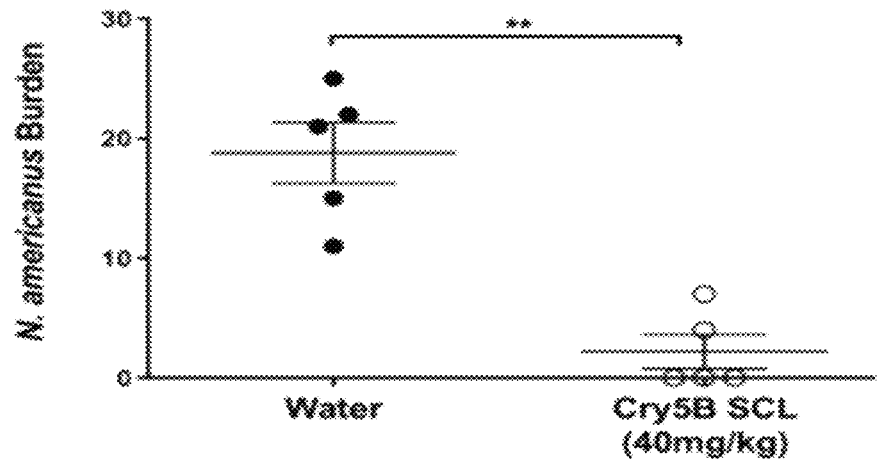
FIG. 11A shows a plot of hookworm burden in hamsters following treatment with either Cry5B spore-crystal lysate (SCL) or water control.
Figure 11B:
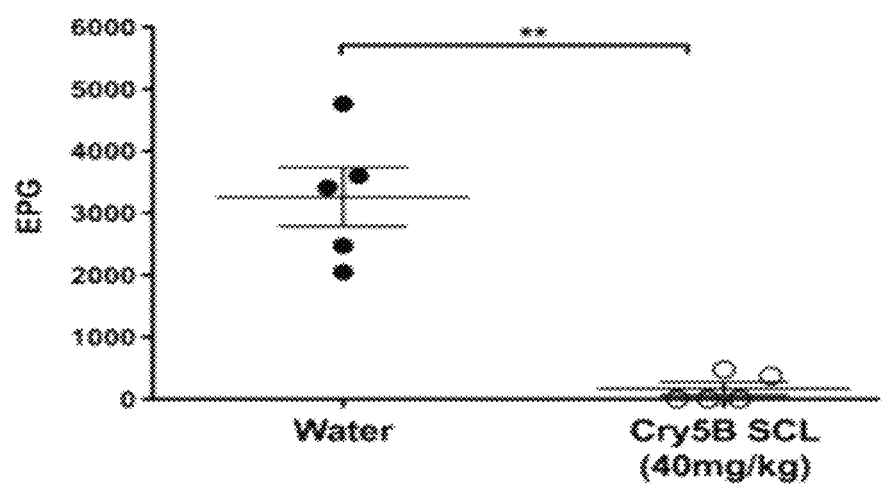
FIG. 11B shows a plot of eggs per gram in hamsters following treatment with either SCL or water control.
Figure 12:
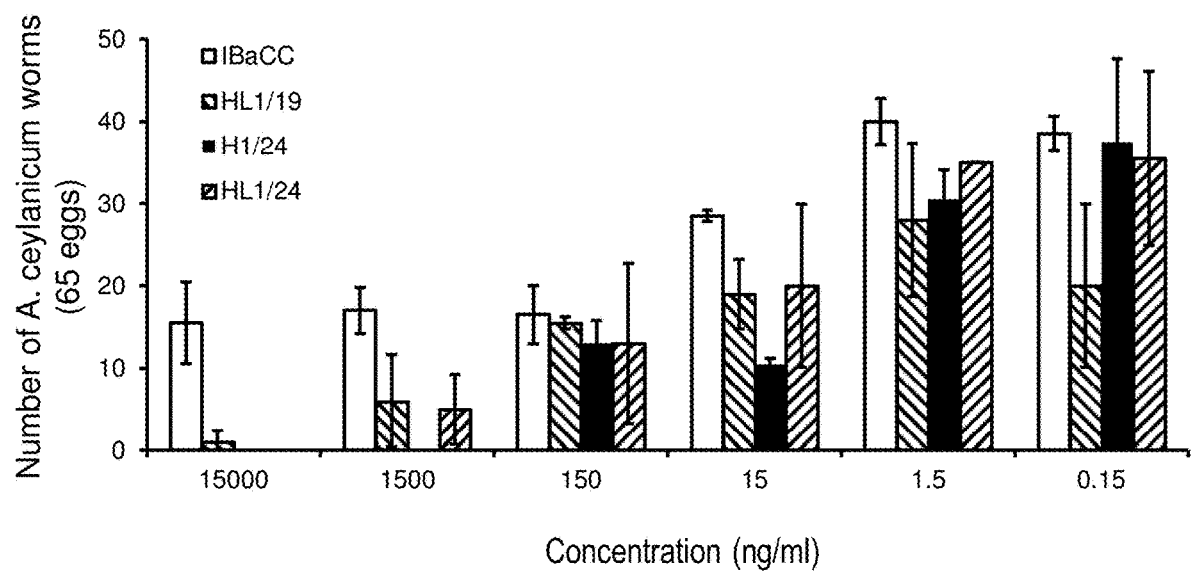
FIG. 12 shows a bar histogram of various concentrations of Cry5B PCC toxicity on *Ancyclostoma ceylanicum* hookworm eggs; some of the Cry5B PCC was treated by the addition of lysozyme.
Figure 13A:
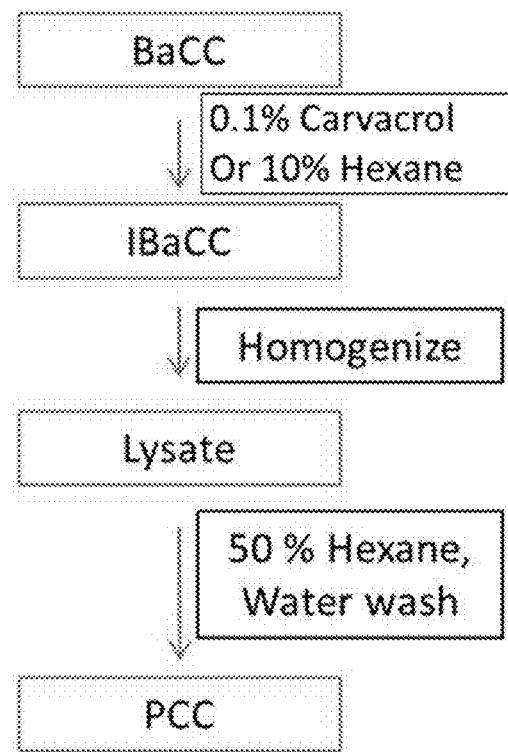
FIG. 13A shows a schematic diagram of the protocol for the purification of PCC from BaCC.
Figure 13B:
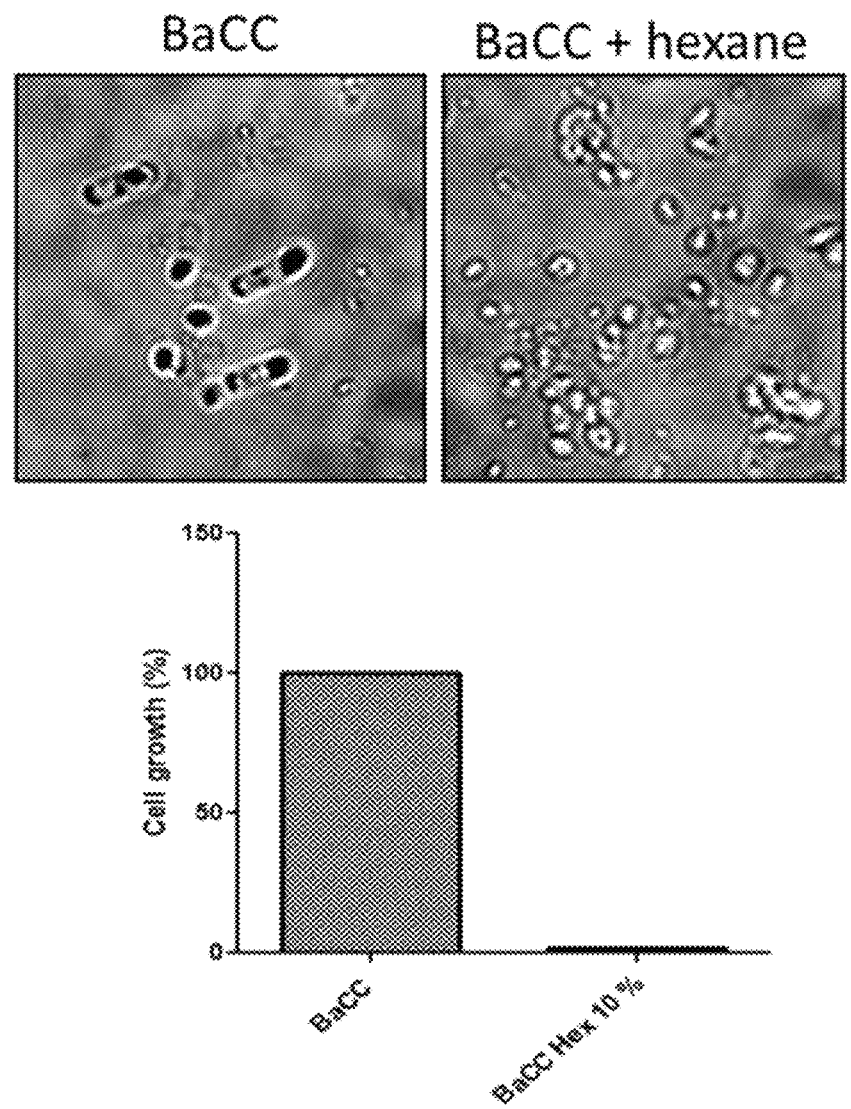
FIG. 13B shows microscopic images of BaCC before and after 10% hexane treatment (top panel), and a bar diagram depicting the percentage of cell growth (measured using OD600) of BaCC before and after 10% hexane treatment (bottom panel).
Figure 13C:
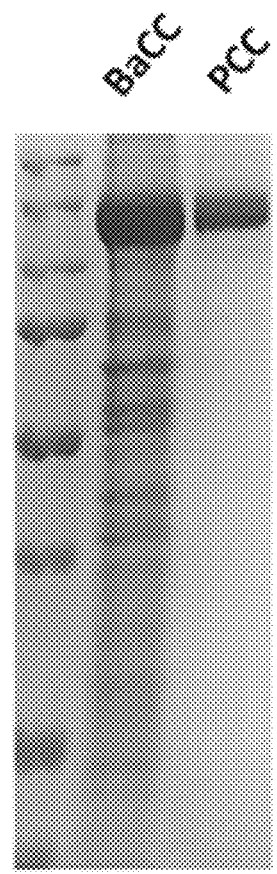
FIG. 13C shows an image of an SDS-PAGE gel depicting the starting BaCC material and the final purified PCC product.

Whipworm mobility in vitro was examined following treatment with PCC made as described in Example 2. Three whipworms were added per well in RPMI medium with antibiotics, 4 wells per dose, and doses of 20, 100, and 500 µg/ml of PCC (Cry5B). FIG. 9A shows a graph of the dose-dependent effect of PCC (Cry5B) on whipworm motility measured at the times indicated. The data is expressed as the average motility index per well, where 3=highly motile, 2=slowly motile, 1=immotile unless touched, 0=immotile even when touched.

Example 5: PCC Reduces Whipworm Burdens In Vivo

The ability of PCC to reduce whipworm burdens in hamsters was examined. Mice were infected with whipworms, *Trichuris muris*. Mice were split into two groups (4 mice per group), water and PCC-oil washed at ~500 mg/kg of Cry5B made as described in Example 2. Both groups were administered water and PCC-oil washed via gavage in 0.5 ml volumes, single dose. Pre-treatment fecal egg counts were measured at day 34 post-infection to place the mice into two groups of equivalent fecal egg counts. Mice were treated by gavage day 35 post-infection. Post-treatment evaluation was conducted on day 41 post-infection (6 days after treatment) in which all mice were opened up and total whipworm counts taken (cecum). There was a 45% reduction in whipworm burdens (average of 5.5 whipworms in water; average of 3 whipworms in PCC), p=0.02.

FIG. 9B shows a histogram of this experiment, comparing whipworm burdens of hamsters treated with water (control) and hamsters treated with 500 mg/kg PCC made as described in Example 2.

Example 6: PCC Intoxicates Hookworms In Vitro

Hookworm (*Necator americanus*) mobility in vitro was examined following treatment with PCC made as described in Example 2. Three hookworms were added per well, 4 wells per dose, at a dose of 250 μg/ml. FIG. 10A shows a graph of changes in hookworm motility over time following in vitro exposure to doses of Cry5B PCC. PCC had a dose-dependent effect on hookworm intoxication. The data is expressed as the average motility index per well, where 3=highly motile, 2=slowly motile, 1=immotile unless touched, 0=immotile even when touched.

Example 7: PCC Reduces Hookworm Burdens In Vivo

PCC was used at a dose of 10 mg/kg to treat hamsters infected with hookworm *Necator americanus*. Six hamsters were infected with *N. americanus* and kept on a regimen of immunosuppression (dexamethasone in the drinking water and twice weekly injections) for the entire duration of the experiment in order to prevent expulsion of the parasites. Following inoculation (approximately 60 days later) three hamsters were treated per os with a single dose of 10 mg/kg of PCC and three hamsters were treated with water as a control. Fecal egg counts were collected before treatment to determine worm loadings and hamsters were grouped into two groups of equivalent fecal egg counts prior to treatment. At 5 days post-treatment, animals were sacrificed and intestinal worm burdens determined.

FIG. 10B shows a histogram of hookworm burdens in hamsters treated with Cry5B PCC and water control. FIG. 10C shows a bar histogram of hookworm fecal egg counts in hamsters before and after treatment with Cry5B PCC and water control. A single PCC dose of 10 mg/kg resulted in a 92% drop in hookworm burden (P=0.016), and a 98% drop in fecal egg count (FEC; P=0.0-19).

In contrast, Cry5B spore-containing lysate (SCL) requires four times the dose to achieve equivalent hookworm burden reduction in hamsters. Hamsters infected with hookworm *Necator americanus* and treated with a single 40 mg/kg dose of Cry5B. FIG. 11A shows a plot of hookworm burden in hamsters following treatment with either Cry5B SCL per os or water control. FIG. 11B shows a plot of eggs per gram in hamsters following treatment with either Cry5B SCL or water control. The single dose of 40 mg/kg Cry5B SCL resulted in an 88% drop in hookworm burden and a 95% drop in fecal egg count.

Example 8: PCC is an Effective Toxin Against Hookworm Eggs

FIG. 12 shows a bar histogram of various concentrations of Cry5B PCC (three preparations) toxicity on *Ancyclostoma ceylanicum* hookworm egg-to-larval development compared to Cry5B IBaCC. Some of the Cry5B PCC was treated by the addition of lysozyme, which did not appear to affect the toxicity of the Cry5B PCC. *A. ceylanicum* eggs (~65/well with multiple wells/dose) were placed in buffer with an *E. coli* food source and allowed to develop 7 days at 25C. The number of eggs that hatch and develop to the third larval infectious stage is noted at day 7. PCC is able to inhibit development of this hookworm even at low concentrations (with an $IC_{50}$ of ~15 ng/mL) and with higher activity than IBaCC.

Example 9: Improved Method for Purification of Purified PCC from BaCC

*B. thuringiensis* expressing Cry5B was fermented as described in Example 1, i.e., (BaCC) at the 10 L scale (Step 631) (FIG. 13A). After 10-fold cell concentration by centrifugation (4,500 rpm, 60 min at 4° C.) (Step 632), the washed BaCC was suspended in 500 ml water (final volume) and hexane was added to 10% v/v final concentration and mixed in a sealed vessel for 1 hour at room temperature to prepare IBaCC (Step 633). FIG. 13B shows microscopic images illustrating the production of IBaCC from BaCC. The microscopic image on the left shows the BaCC, and the microscopic image on the right shows the effect of hexane on BaCC, with the rod-structure destroyed. The bar graph of FIG. 13B shows the quantification of the percentage cell growth of BaCC (100% cell growth) and BaCC treated with 10% hexane (0% cell growth, complete inactivation). FIG. 13C shows an image of an SDS-PAGE gel, depicting the starting BaCC material and the final purified PCC product, following the process depicted in the diagram of FIG. 13A. Other methods of cell inactivation, e.g., surfactants, microbicides, biocides, etc., can substitute for hexane.

Purified Cry5B Crystals (PCC) were produced from IBaCC as described in Example 2. Briefly, IBaCC was homogenized at 15,000 psi for 5 to 7 passes to lyse the cells, releasing the PCC from the IBaCC cell wall ghosts (Step 634).

To purify the PCC by phase-partioning from the soluble cell components, lipids, and cell wall debris, hexane was added to 50% v/v and mixed vigorously in a sealed vessel for 1 hour at room temperature. The emulsion was transferred to sealed bottles and centrifuged at 4,500 rpm for 1 hour at 4° C. (Step 635) The upper hexane layer was collected and transferred to solvent waste. The interface layer containing cell wall debris was removed and discarded. The aqueous layer containing water-soluble cellular constituents was removed and discarded, and the PCC in the pellet was retained. Following water washing the PCC pellets were stored frozen. The resulting PCC had 98% protein w/w. Other methods of PCC recovery, such as continuous centrifugation to collect the PCC in the aqueous phase and the hexane and interface in the supernatant phase are possible. The final PCC can be stored frozen or lyophilized or spray dried and stored at room-temperature, 4° C., or frozen.

Figure 14:
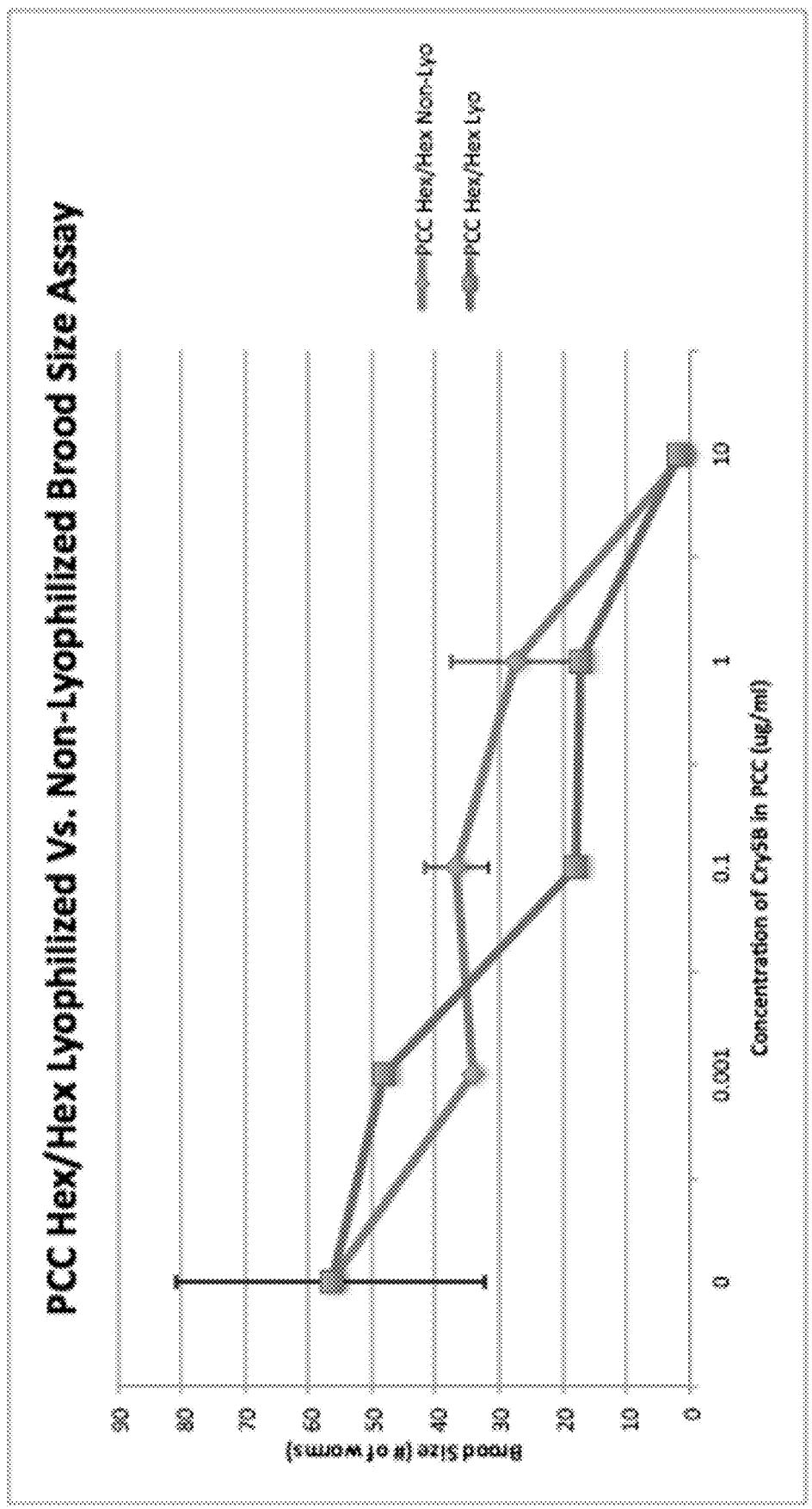
FIG. 14 shows a line graph depicting the bioactivity of PCC processed from BaCC with 10% hexane to kill the bacterium and 50% hexane to remove other bacterial contaminants (PCC-Hex/Hex).

Example 10: PCC Purified by the Improved Method is an Effective Toxin Against Nematodes In another example, the method of Example 9 was combined with the hexane phase partitioning method of Example 9. FIG. 14 shows a graph of the bioactivity of PCC processed from BaCC with 10% hexane to kill the bacterium and 50% hexane to remove other bacterial contaminants (PCC-Hex/Hex). The non-lyophilized PCC is shown on the graph as diamonds and the lyophilized PCC is shown as squares. The readout is the average three-day brood size of a single *C. elegans* starting at the larval stage L4 (n=3 per condition). The PCC efficacy is excellent since at 10 µg/mL there is complete inhibition of brood size production. In comparison, published data indicates an average 70% inhibition at this dose (Hu, Y, et al., Proc Natl Acad Sci USA 107: 5955-60 (2010)). These data demonstrate that the PCC Hex/Hex process is fully compatible with lyophilization.

Figure 15:
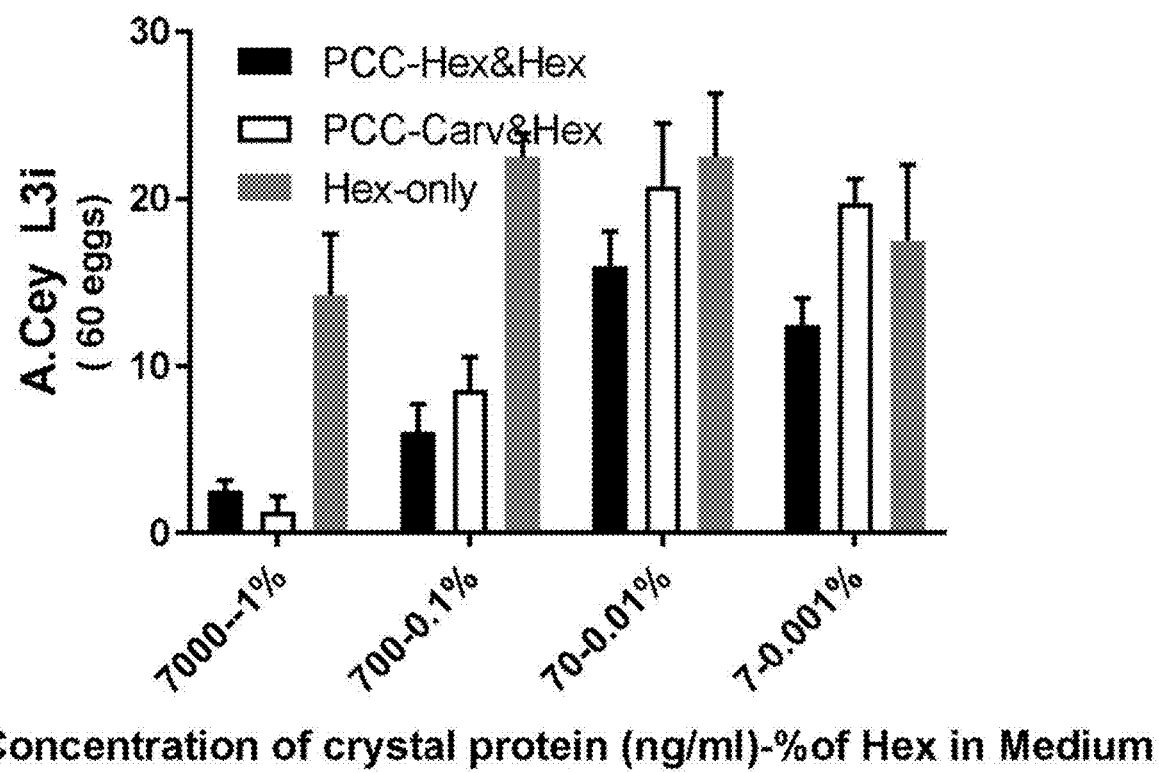
FIG. 15 shows a bar graph depicting the bioactivity of PCC processed from BaCC with carvacrol to kill the bacterium (IBaCC), with 50% hexane to remove other bacterial contaminants (PCC-Carv&Hex), and with 10% hexane to kill the bacterium and 50% hexane to remove other bacterial contaminants (PCC-Hex&Hex).
Figure 16:
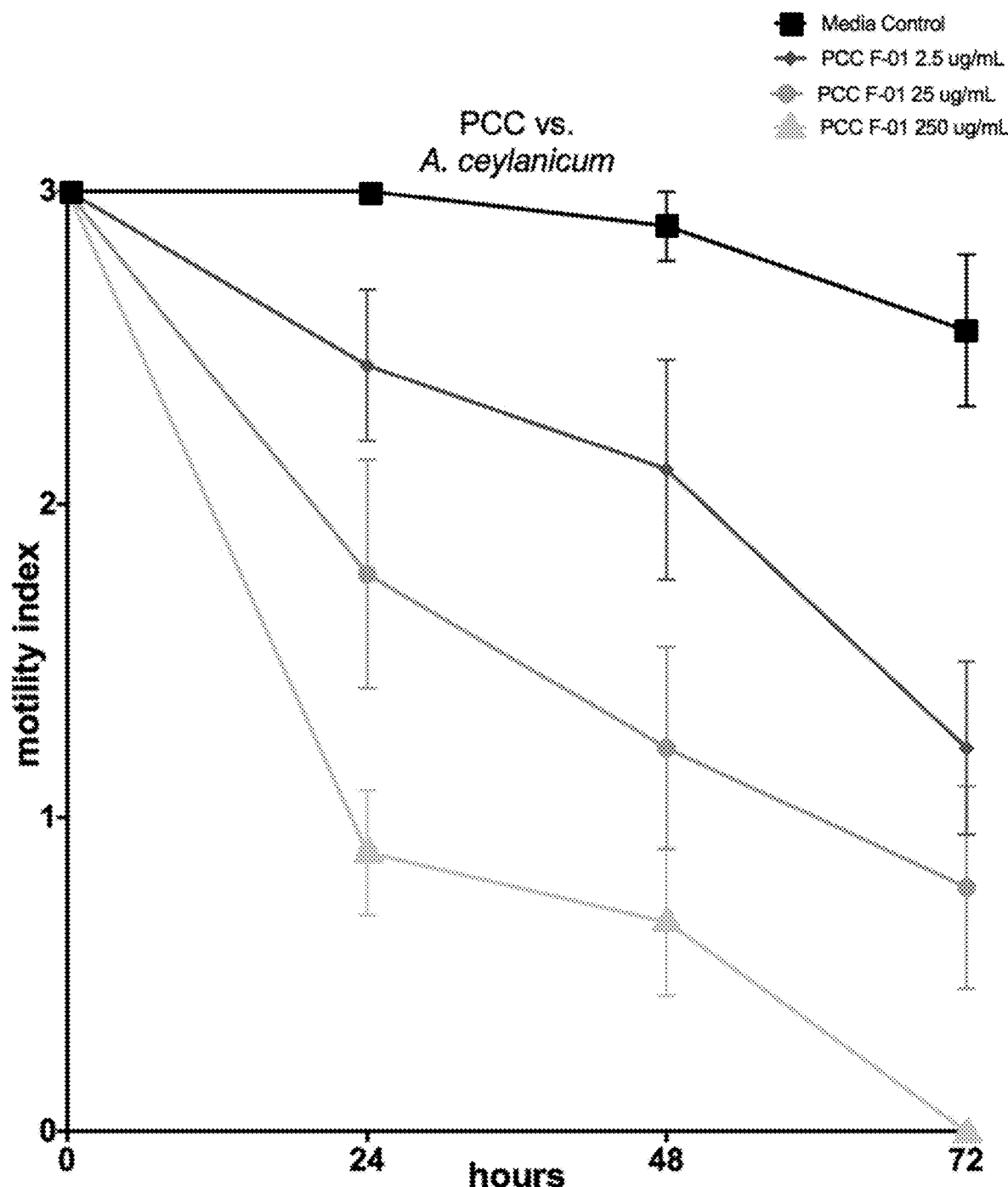
FIG. 16 shows a line graph depicting the bioactivity of PCC processed from BaCC with carvacrol to kill the bacterium and 50% hexane to remove other bacterial contaminants.

Example 11: PCC Purified by the Improved Method is an Effective Toxin Against Hookworms FIG. 15 shows the bioactivity of PCC processed from BaCC with carvacrol to kill the bacterium (IBaCC), and 50% hexane phase partitioning to remove other bacterial contaminants (PCC-Carv&Hex). The readout is the percent of hookworm *A. ceylanicum* eggs that reach mature infectious larval stage at 7 days. A lower bar indicates more inhibition of hookworm growth and development, and is indicative of intoxication. Control is hexane only in the medium at the same final concentration as in the sample with PCC. The data show that hexane alone has no effect on the parasites.

FIG. 16 shows the bioactivity of PCC processed from BaCC with carvacrol to kill the bacterium and 50% hexane to remove other bacterial contaminants. The readout is motility of hookworm *A. ceylanicum* adults in vitro scored every 24 hours, where 3=active and highly motile; 2=slowly motile; 1=immotile unless touched (highly intoxicated); 0=immotile even when touched (presumably dead). The data show a clear dose-response with increasing doses of PCC resulting in decreasing motility, demonstrating that the PCC processed via hexane is highly bioactive.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While particular steps, elements, embodiments and applications of the present invention have been shown and described herein for purposes of illustration, it will be understood, of course, that the invention is not limited thereto since modifications may be made by persons skilled in the art, particularly in light of the foregoing teachings, without deviating from the spirit and scope of the invention. Accordingly, the invention is not limited except as by the appended claims.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

SEQUENCE LISTING

```
Sequence total quantity: 24
SEQ ID NO: 1             moltype = AA  length = 1245
FEATURE                  Location/Qualifiers
source                   1..1245
                         mol_type = protein
                         organism = Bacillus thuringiensis
SEQUENCE: 1
MATINELYPV PYNVLAHPIK EVDDPYSWSN LLKGIQEGWE EWGKTGQKKL FEDHLTIAWN  60
LYKTGKLDYE ALTKASISLI GFIPGAEAAV PFINMEVDFV WPKLFGANTE GKDQQLFNAI  120
MDAVNKMVDN KFLSYNLSTL NKTIEGIQGN LGLFQNAIQV AICQGSTPER VNFDQNCTPC  180
NPNQPCKDDL DRVASRFDTA NSQFTQHLPE FKNPWSDENS TQEFKRTSVE LTLPMYTTVA  240
TLHLLLYEGY IEFMTKWNFH NEQYLNNLKV ELQQLIHSYS ETVRTSFLQF LPTLNNRSKS  300
SVNAYNRYVR NMTVNCLDIA ATWPTFDTHN YHQGGKLDLT RIILSDTAGP IEEYTTGDKT  360
SGPEHSNITP NNILDTPSPT YQHSFVSVDS IVYSRKELQQ LDIATYSTNN SNNCHPYGLR  420
LSYTDGSRYD YGDNQPDFTT SNNNYCHNSY TAPITLVNAR HLYNAKGSLQ NVESLVVSTV  480
NGGSGSCICD AWINYLRPPQ TAKNESFPDQ KDNVLYPITE TVNKGTGGNL GVISAYVPME  540
LVPENVIGDV NADTKLPLTQ LKGFPFEKYG SEYNNRGISL VREWINGNNA VKLSNSQSVG  600
IQITNQTEQK YEIRCRYASK GDNNVYFNVD LSENPFRNSI SFGSTESSVV GVQGENGKYI  660
LKSITTVEIP AGSFYVHITN QGSSDLFLDR IEFVPKIQFQ FCDNNNLHCD CNNPVDTDCT  720
FCCVCTSLTD CDCNNPRGLD CTLCCQVENQ LPSFVTLTDL QNITTQVNAL VASSEHDTLA  780
TDVSDYEIEE VVLKVDALSG EVFGKEKKAL RKLVNHTKRL SKARNLLIGG NFDNLDAWYR  840
GRNVVNVSDH ELFKSDHYLL PPPTLYSSYM FQKVEESKLK ANTRYSVSGF IAHAEDLEIV  900
```

```
VSEYGQEVKK VVQVPYGEAF PLTSRGAICC PPRSTSNGKP ADPHEFSYSI DVGTLDVEAN  960
PGIELGLRIV ERTGMARYSN LEIREDPPLK KNELRNVQRA ARNWRSAYDQ ERAEVTALIQ  1020
PVLNQINALY ENEDWNGAIR SGVSYHDLEA IVLPTLPKLN HWFMSDMLGE QGSILAQFQE  1080
ALDRAYTQLE ESTILHNGHF TTDAANWTIE GDAHHAILED GRRVLRLPDW SSSVSQTIEI  1140
ENFDPDKEYQ LVFHAQGEGT VSLQHGEEGE YVETHPHKSA NFTTSHRQGL TFETNKVTVE  1200
ITSEDGEFLV DHIALVEAPL PTDDQSSDGN TFSNTNSNTS MNNNQ                  1245

SEQ ID NO: 2           moltype = AA  length = 803
FEATURE                Location/Qualifiers
source                 1..803
                       mol_type = protein
                       organism = Bacillus thuringiensis
SEQUENCE: 2
MTCQLQAQPL IPYNVLAGYP TSNTGSPIGN AGNQFDQFEQ TVKELKEAWE AFQKNGSFSL  60
AALEKGFDAA IGGGSFDYLG LVQAGLGLVG TLGAAIPGVS VAVPLISMLV GVFWPKGTNN  120
QENLITVIDK EVQRILDEKL SDQLIKKINA DLNAFTDLVT RLEEVIIDAT FENHKPVLQV  180
SKSNYMKVDS AYFSTGGILT LGMSDFLTDT YSKLTFPLYV LGATMKLSAY HSYIQFGNTW  240
LNKVYDLSSD EGKTMSQALA RAKQHMRQDI AFYTSQALNM FTGNLPSLSS NKYAINDYNV  300
YTRAMVLNGL DIVATWPTLY PDDYSSQIKL EKTRVIFSDM VGQSESRDGS VTIKNIFDNT  360
DSHQHGSIGL NSISYFPDEL QKAQLRMYDY NHKPYCTDCF CWPYGVILNY NKNTFRYGDN  420
DPGLSGDVQL PAPMSVVNAQ TQTAQYTDGE NINTDTGRSW LCTLRGYCTT NCFPGRGCYN  480
NSTGYGESCN QSLPGQKIHA LYPFTQTNVL GQSGKLGLLA SHIPYDLSPN NTIGDKDTDS  540
TNIVAKGIPV EKGYASSGQK VEIIREWING ANVVQLSPGQ SWGMDFTNST GGQYMVRCRY  600
ASTNDTPIFF NLVYDGGSNP IYNQMTFPAT KETPAHDSVD NEILGIKGIN GNYSLMNVKD  660
SVELPSGKFH VFFTNNGSSA IYLDRLEFVP LDQPAAPTQS TQPINYPITS RLPHRSGEPP  720
AIIWEKSGNV RGNQLTISAQ GVPENSQIYL SVGGDRQILD RSNGFKLVNY SPTYSFTNIQ  780
ASSSNLVDIT SGTITGQVQV SNL                                          803

SEQ ID NO: 3           moltype = AA  length = 1186
FEATURE                Location/Qualifiers
source                 1..1186
                       mol_type = protein
                       organism = Bacillus thuringiensis
SEQUENCE: 3
MDCNLQSQQN IPYNVLAIPV SNVNALVDTA GDLKKAWEEF QKTGSFSLTA LQQGFSASQG  60
GAFNYLTLLQ SGISLAGSFV PGGTFVAPIV NMVIGWLWPH ENKTADTENL IKLIDEEIQK  120
QLNKALLDQD RNNWTSFLES IFDTSATVSN ADIDAQWSGT VDTTNRQQKT PTTSDYLNVV  180
GKFDSADSSI ITNENQIMNG NFDVAAAPYF VDGATLRLSL YQSYIKFCNS WIDAVGFSTN  240
DANTQKANLA RTKLTMRSTI NEYTQRVMKV FKDSKNMPTI GTNKFSVDAY NVYVKGMTLN  300
VLDMVAIWSS LYPNDYTSQT AIEQTRVTFS NMVGQEEGTD GTLKIYNTFD SLSYQHSLIP  360
NNNVNLISYY TDELQNLELA VYTPKGGSGY AYPYGFILNY ANSNYKYGDN DPTGKPLNKQ  420
DGPIQQINAA TQNSKYLDGE TINGIGASLP GYCTTGSSAT EQPFSCTGTA NSYKASCNPS  480
DTNQKINALY AFTQTNVKGS TGKLGVLASL VPYDLNPKNV FGELDSDTNN VILKGIPAEK  540
GYFPNNARPT VVKEWINGAS AVPFYSGNTL FMTATNLTAT QYKIRIRYAN PNSDTQISVL  600
ITQNGSQISN SNLTLYSTTD SSMSSNLPQN VYVTGENGNY TLLDLYSTTN VLSTGDITLK  660
LTGGNQKIFI DRIEFIPTMP VPAPTNNTNN NNGDNGNNNP PHHGCAIAGT QQLCSGPPKF  720
EQVSDLEKIT TQVYMLFKSS SYEELAIKVS SYQINQVALK VMALSDEKFC EEKRLLRKLV  780
NKANQLLEAR NLLVGGNFET TQNWVLGTNA YDNYDSFLFN GNYLSLQPAS GFFTSYAYQK  840
IDESTLKPYT RYKVSGFIGQ SNQVELIISR YGKEIDKILN VPYAGPLPIT ADASITCCAP  900
EIDQCDGGQS DSHFFNYSID VGALHPELNP GDEIGLKIVQ SNGYISISNL EIIEERPLTE  960
MEIQAVNRKD QKWKRELLLE CASVSELLQP IDNQIDSLFK DANWYNDILP HVTYQTLKNI  1020
IVPDLPKLKH WFIDHLPGEY HEIEQKMKEA LKHAFTQLDE KNLIHNGHFA TNLIDWQVEG  1080
DAFMKVLENN ALALQLSNWD SSVSQSIDIL EFDEDKAYKL RVYAQGSGTI QFGNCEDEAI  1140
QFNTNSFVYK EKIIYFDSPS INLHIQSEGS EFVVSSIDLV ELSDDE                 1186

SEQ ID NO: 4           moltype = AA  length = 1167
FEATURE                Location/Qualifiers
source                 1..1167
                       mol_type = protein
                       organism = Bacillus thuringiensis
SEQUENCE: 4
MTNPTILYPS YHNVLAHPIR LDSFFDPFVE TFKDLKGAWE EFGKTGYMDP LKQHLQIAWD  60
TSQNGTVDYL ALTKASISLI GLIPGADAVV PFINMFVDFI FPKLFGRGSQ QNAQAQFFEL  120
IIEKVKELVD EDFRNFTLNN LLNYLDGMQT ALSHFQNDVQ IAICQGEQPG LMLDQTPTAC  180
TPTTDHLISV RESFKDARTT IETALPHFKN PNLSTNDNTP DFNSDTVLLT LPMYTTGATL  240
NLILHQGYIQ FAERWKSVNY DESFINQTKV DLQRRIQDYS TTVSTTFEKF KPTLNPSNKE  300
SVNKYNRYVR SMTLQSLDIA ATWPTLDNVN YPSNVDIQLD QTRLVFSDVA GPWEGNDNIT  360
SNIIDVLTPI NTGIGFQESS DLRKFTYPRI ELQSMQFHGQ YVNSKSVEHC YSDGLKLNYK  420
NKTITAGVSN IDESNQNNKH NYGPVINSPI TDINVNSQNS QYLDLNSVMV NGGQKVTGCS  480
PLSSNGNSNN AALPNQKINV IYSVQSNDKP EKHADTYRKW GYMSSHIPYD LVPENVIGDI  540
DPDTKQPSLL LKGFPAEKGY GDSIAYVSEP LNGANAVKLT SYQVLQMEVT NQTTQKYRIR  600
IRYATGGDTA ASIWFHIIGP SGNDLTNEGH NFSSVSSRNK MFVQGNNGKY VLNILTDSIE  660
LPSGQQTILI QNTNSQDLFL DRIEFISLPS TSTPTSTNFV EPESLEKIIN QVNQLFSSSS  720
QTELAHTVSD YKIDQVVLKV NALSDDVFGV EKKALRKLVN QAKQLSKARN VLVGGNFEKG  780
HEWALSREAT MVANHELFKG DHLLLPPPTL YPSYAYQKID ESKLKSNTRY TVSGFIAQSE  840
HLEVVVSRYG KEVHDMLDIP YEEALPISSD ESPNCCKPAA CQCSSCDGSQ SDSHFFSYSI  900
DVGSLQSDVN LGIEFGLRIA KPNGFAKISN LEIKEDRPLT EKEIKKVQRK EQKWKKAFNQ  960
EQAEVATTLQ PTLDQINALY QNEDWNGSVH PASDYQHLSA VVVPTLPKQR HWFMEGREGE  1020
HVVLTQQFQQ ALDRAFQQIE EQNLTHNGNL ANGLTDWTVT GDAQLTIFDE DPVLELAHWD  1080
```

-continued

```
ASISQTIEIM DFEGRHRIQT ACTWKRQRNS YRSTWRKRLE TMTFNTTSFT TQEQTFYFEG  1140
DTVDVHVQSE NNTFLIDSVE LIEIIEE                                      1167

SEQ ID NO: 5            moltype = AA  length = 1167
FEATURE                 Location/Qualifiers
source                  1..1167
                        mol_type = protein
                        organism = Bacillus thuringiensis
SEQUENCE: 5
MTNPTILYPS YHNVLAHPIR LDSFFDPFVE TFKDLKSAWE EFGKTGYMDP LKQHLQIAWD  60
TSQNGTVDYL ALTKASISLI GLIPGADAVV PFINMFVDFI FPKLFGRGSQ QNAQAQFFEL  120
IIEKVKELVD EDFRNFTLNN LLNYLDGMQT ALSHFQNDVQ IAICQGEQPG LMLDQTPTAC  180
TPTTDHLISV RESFKDARTT IETALPHFKN PNLSTNDNTP DFNSDTVLLT LPMYTTAATL  240
NLILHQGYIQ FAERWKSVNY DESFINQTKV DLQRRIQDYS TTVSTTFEKF KPTLNPSNKE  300
SVNKYNRYVR SMTLQSLDIA ATWPTLDNVN YPSNVDIQLD QTRLVFSDVA GPWEGNDNIT  360
SNIIDVLTPI NTGIGFQESS DLRKFTYPRI ELQSMQFHGQ YVNSKSVEHC YSDGLKLNYK  420
NKTITAGVSN IDESNQNNKH NYGPVINSPI TDINVNSQNS QYLDLNSVMV NGGQKVAGCS  480
PLSSNGNSNN AALPNQKINV IYSVQSNDKP EKHADTYRKW GYMSSHIPYD LVPENVIGDI  540
DPDTKQPSLL LKGFPAEKGY GDSIAYVSEP LNGANAVKLT SYQVLKMEVT NQTTQKYRIR  600
IRYATGGDTA ASIWFHIIGP SGNDLTNEGH NFSSVSSRNK MFVQGNNGKY VLNILTDSIE  660
LPSGQQTILI QNTNSQDLFL DRIEFISLPS TSTPTSTNFV EPESLEKIIN QVNQLFSSSS  720
QTELAHTVSD YKIDQVVLKV NALSDDVFGV EKKALRKLVN QAKQLSKARN VLVGGNFEKG  780
HEWALSREAT MVANHELFKG DHLLLPPPTL YPSYAYQKID ESKLKSNTRY TVSGFIAQSE  840
HLEVVVSRYG KEVHDMLDIP YEEALPISSD ESPNCCKPAA CQCSSCDGSQ SDSHFFSYSI  900
DVGSLQSDVN LGIEFGLRIA KPNGFAKISN LEIKEDRPLT EKEIKKVQRK EQKWKKAFNQ  960
EQAEVATTLQ PTLDQINALY QNEDWNGSVH PHVTYQHLSA VVVPTLPKQR HWFMEDREGE  1020
HVVLTQQFQQ ALDRAFQQIE EQNLIHNGNF ANGLTDWTVT GDAQLSIFDE DPVLELAHWD  1080
ASISQTIEIM DFEEDTEYKL RVRGKGKGTV TVQHGEEELE TMTFNSTSFT TQEQTFYFEG  1140
DTVDVHVQSE NNTFLIDSVE LIEIIEE                                      1167

SEQ ID NO: 6            moltype = AA  length = 475
FEATURE                 Location/Qualifiers
source                  1..475
                        mol_type = protein
                        organism = Bacillus thuringiensis
SEQUENCE: 6
MIIDSKTTLP RHSLIHTIKL NSNKKYGPGD MTNGNQFIIS KQEWATIGAY IQTGLGLPVN  60
EQQLRTHVNL SQDISIPSDF SQLYDVYCSD KTSAEWWNKN LYPLIIKSAN DIASYGFKVA  120
GDPSIKKDGY FKKLQDELDN IVDNNSDDDA IAKAIKDFKA RCGILIKEAK QYEEAAKNIV  180
TSLDQFLHGD QKKLEGVINI QKRLKEVQTA LNQAHGESSP AHKELLEKVK NLKTTLERTI  240
KAEQDLEKKV EYSFLLGPLL GFVVYEILEN TAVQHIKNQI DEIKEQLDSA QHDLDRDVKI  300
IGMLNSINTD IDNLYSQGQE AIKVFQKLQG IWATIGAQIE NLRTTSLQEV QDSDDADEIQ  360
IELEDASDAW LVVAQEARDF TLNAYSTNSR QNLPINVISD SCNCSTTNMT SNQYSNPTTN  420
MTSNQYMISH EYTSLPNNFM LSRNSNLEYK CPENNFMIYW YNNSDWYNNS DWYNN        475

SEQ ID NO: 7            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 7
VYIDRIEFVP                                                         10

SEQ ID NO: 8            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 8
VYIDKIEFIP                                                         10

SEQ ID NO: 9            moltype = AA  length = 10
FEATURE                 Location/Qualifiers
REGION                  1..10
                        note = Description of Artificial Sequence: Synthetic peptide
source                  1..10
                        mol_type = protein
                        organism = synthetic construct
SEQUENCE: 9
VLIDKIEFLP                                                         10

SEQ ID NO: 10           moltype = AA  length = 10
FEATURE                 Location/Qualifiers
REGION                  1..10
                        note = Description of Artificial Sequence: Synthetic peptide
```

```
source                    1..10
                          mol_type = protein
                          organism = synthetic construct
SEQUENCE: 10
VFLDRIEFIP                                                              10

SEQ ID NO: 11             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 11
LFLDRIEFVP                                                              10

SEQ ID NO: 12             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 12
FYVDSIEFIP                                                              10

SEQ ID NO: 13             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 13
VYIDRIEFIP                                                              10

SEQ ID NO: 14             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 14
VYVDRIEFIP                                                              10

SEQ ID NO: 15             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 15
IYIDKIEFIP                                                              10

SEQ ID NO: 16             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 16
MVLDRIEFVP                                                              10

SEQ ID NO: 17             moltype = AA  length = 10
FEATURE                   Location/Qualifiers
REGION                    1..10
                          note = Description of Artificial Sequence: Synthetic peptide
source                    1..10
                          mol_type = protein
                          organism = synthetic construct
SEQUENCE: 17
IYLDRLEFVP                                                              10

SEQ ID NO: 18             moltype = AA  length = 10
FEATURE                   Location/Qualifiers
REGION                    1..10
```

```
                         note = Description of Artificial Sequence: Synthetic peptide
source                   1..10
                         mol_type = protein
                         organism = synthetic construct
SEQUENCE: 18
IFIDRIEFIP                                                                          10

SEQ ID NO: 19            moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 19
LILDKIEFLP                                                                          10

SEQ ID NO: 20            moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 20
FVLDKIELIP                                                                          10

SEQ ID NO: 21            moltype = AA  length = 10
FEATURE                  Location/Qualifiers
REGION                   1..10
                         note = Description of Artificial Sequence: Synthetic peptide
source                   1..10
                         mol_type = protein
                         organism = synthetic construct
SEQUENCE: 21
LFLDRIEFIS                                                                          10

SEQ ID NO: 22            moltype = AA  length = 9
FEATURE                  Location/Qualifiers
REGION                   1..9
                         note = Description of Artificial Sequence: Synthetic peptide
source                   1..9
                         mol_type = protein
                         organism = synthetic construct
SEQUENCE: 22
IIDKIEFIP                                                                           9

SEQ ID NO: 23            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 23
DRIEF                                                                               5

SEQ ID NO: 24            moltype = AA  length = 5
FEATURE                  Location/Qualifiers
REGION                   1..5
                         note = Description of Artificial Sequence: Synthetic peptide
source                   1..5
                         mol_type = protein
                         organism = synthetic construct
SEQUENCE: 24
DRLEF                                                                               5
```

What is claimed is:

1. A method of treating a parasitic worm or helminth infection in a subject comprising:
    administering to the subject a therapeutically effective amount of a pharmaceutical composition comprising isolated native, bioactive nematicidal crystals formed from a single type of nematicidal crystal protein,
    wherein the bioactive nematicidal crystals are produced by a non-sporulating form of host bacterium, and
    wherein the pharmaceutical composition is substantially free of any bacterial spores or host bacterial proteins other than nematicidal crystal protein in the form of a crystal.

2. The method of claim 1, wherein the nematicidal crystal protein is selected from the group consisting of Cry5B, Cry13A, Cry14A, and Cry21A, or a bioactive variant or truncation thereof that has at least 90% of the toxic activity of a corresponding wild-type protein.

3. The method of claim 1, wherein the nematicidal crystal protein is Cry5B.

4. The method of claim 1, wherein the nematicidal crystal protein is Cry5B variant Ser407Cys.

5. The method of claim 1, wherein the pharmaceutical composition further comprises a second crystal protein in the form of an isolated native, bioactive nematicidal crystal formed from only the second crystal protein.

6. The method of claim 1, wherein the pharmaceutical composition comprises at least about 95% isolated native, bioactive nematicidal crystal content.

7. The method of claim 1, wherein the pharmaceutical composition is in a dry powdered form and is encapsulated by a pharmaceutical capsule.

8. The method of claim 1, wherein the non-sporulating host bacterium is a *Bacillus* species.

9. The method of claim 1, wherein the non-sporulating host bacterium is *Bacillus thuringiensis* (Bt), an *E. coli* species or a *P. flurorescens* species.

10. The method of claim 1, wherein the non-sporulating host bacterium is genetically engineered to have a genetic mutation that results in a defect in sporulation such that the native, bioactive nematicidal crystal is trapped in the cytosol of the bacterium.

11. The method of claim 10, wherein the genetic mutation resulting in a defect of sporulation is the deletion or inactivation of gene spo0A.

12. The method of claim 1, wherein the non-sporulating host bacterium is genetically engineered to express the single type of nematicidal crystal protein under the control of a non-sporulation specific promoter.

13. The method of claim 12, wherein the non-sporulation specific promoter is a Cry3A, GerA, GNAT, or TadA promoter.

14. The method of claim 1, wherein the non-sporulating host bacterium is exposed to an antimicrobial compound to inactivate the host bacterium,
optionally wherein the antimicrobial compound is iodine, a pharmaceutical antibiotic, a beta lactam antibiotic, or an organic solvent.

15. The method of claim 14, wherein a food-grade oil is added to the inactivated host bacterium to extract the antimicrobial compound, soluble cell components, lipids, and cell wall debris from the nematicidal crystal protein.

16. The method of claim 14, wherein an organic solvent is added to the inactivated host bacterium to extract the antimicrobial compound from the nematicidal crystal protein.

17. The method of claim 14, wherein the inactivated host bacterium is homogenized to form a bacterial lysate that includes the native, bioactive nematicidal crystals.

18. The method of claim 1, wherein the subject is a mammal.

19. The method of claim 1, wherein the pharmaceutical composition is suitable for oral administration.

20. The method of claim 10, wherein one or more genes selected from the group consisting of spo0B, spo0E, spo0F, spo0J and spo0M, or a combination thereof, are mutated.

21. The method of claim 10, wherein one or more genes selected from the group consisting of spoIIB, spoIID, spoIIE, spoIIF, spoIIG, spoIIL and spoIIM, or a combination thereof, are mutated.

22. The method of claim 10, wherein one or more genes selected from the group consisting of spoIIIA, spoIIIB and spoIIIE, or a combination thereof, are mutated.

23. The method of claim 10, wherein one or more genes selected from the group consisting of spoIVA, spoIVC and spoIVD, or a combination thereof, are mutated.

24. The method of claim 10, wherein one or more genes selected from the group consisting of spoVG, spoVK, spoVL, spoVM, spoVN, spoVP and spoVQ, or a combination thereof, are mutated.

25. The method of claim 10, wherein spoVID is mutated.

26. The method of claim 10, wherein one or more genes selected from the group consisting of σH, σF, σE, σG and σK, or a combination thereof, are mutated.

27. The method of claim 1, wherein the nematicidal crystal protein is Cry5B or a bioactive variant or truncation thereof that has at least 90% of the toxic activity of a corresponding wild-type protein.

28. The method of claim 1, wherein the nematicidal crystal protein is Cry5C, Cry5D or a bioactive variant or truncation thereof that has at least 90% of the toxic activity of a corresponding wild-type protein.

29. The method of claim 1, wherein the nematicidal crystal protein is Cry6A or a bioactive variant or truncation thereof that has at least 90% of the toxic activity of a corresponding wild-type protein.

30. The method of claim 1, wherein the nematicidal crystal protein is Cry21B or a bioactive variant or truncation thereof that has at least 90% of the toxic activity of a corresponding wild-type protein.

31. The method of claim 1, wherein the nematicidal crystal protein is Cry55B or a bioactive variant or truncation thereof that has at least 90% of the toxic activity of a corresponding wild-type protein.

32. A method of treating a parasitic worm or helminth infection in a subject comprising:
administering to the subject a therapeutically effective amount of a pharmaceutical composition comprising isolated native, bioactive nematicidal crystals formed from a single type of nematicidal crystal protein,
wherein the nematicidal crystal protein is Cry5B,
wherein the bioactive nematicidal crystals are produced by a non-sporulating form of host bacterium, and
wherein the pharmaceutical composition is substantially free of any bacterial spores or host bacterial proteins other than nematicidal crystal protein in the form of a crystal.

33. A method of treating a parasitic worm or helminth infection in a subject comprising:
administering to the subject a therapeutically effective amount of a pharmaceutical composition comprising isolated native, bioactive nematicidal crystals formed from a single type of nematicidal crystal protein,
wherein the nematicidal crystal protein is Cry5B variant Ser407Cys,
wherein the bioactive nematicidal crystals are produced by a non-sporulating form of host bacterium, and
wherein the pharmaceutical composition is substantially free of any bacterial spores or host bacterial proteins other than nematicidal crystal protein in the form of a crystal.

* * * * *